(12) United States Patent
Chappell et al.

(10) Patent No.: US 9,487,762 B1
(45) Date of Patent: Nov. 8, 2016

(54) METHOD AND SYSTEM FOR PRODUCING TRITERPENES

(71) Applicant: University of Kentucky Research Foundation, Lexington, KY (US)

(72) Inventors: Joe Chappell, Lexington, KY (US); Thomas D. Niehaus, Lexington, KY (US); Shigeru Okada, Tokyo (JP); Timothy P. Devarenne, Bryan, TX (US); David S. Watt, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 14/050,020

(22) Filed: Oct. 9, 2013

Related U.S. Application Data

(60) Provisional application No. 61/711,654, filed on Oct. 9, 2012.

(51) Int. Cl.
*C12N 9/10* (2006.01)

(52) U.S. Cl.
CPC .................................. *C12N 9/1007* (2013.01)

(58) Field of Classification Search
CPC ...................................................... C12N 9/1007
See application file for complete search history.

(56) References Cited

U.S. PATENT DOCUMENTS

2010/0009423 A1* 1/2010 Chappell et al. ............. 435/167

OTHER PUBLICATIONS

Liscombe et al., PNAS USA, 107(44), 18793-18798, 2010.*
Han et al., Genetics, 176, 2625-2635, 2007.*
Brown, A. C., Knights, B. A., and Conway, E. (1969) Phytochemistry 8, 543-547.
Derenne, S., Largeau, C., Hetenyi, M., BruknerWein, A., Connan, J., and Lugardon, B. (1997) Geochimica Et Cosmochimica Acta 61, 1879-1889.
Glikson, M., Lindsay, K., and Saxby, J. (1989) Organic Geochemistry 14, 595-608.
Mastalerz, M., and Hower, J. C. (1996) Organic Geochemistry 24, 301-308.
Metzger, P., and Largeau, C. (2005) Applied Microbiology and Biotechnology 66, 486-496.
Gelpi, E., Oro, J., Schneide.Hj, and Bennett, E. O. (1968) Science 161, 700-702.
Metzger, P., Allard, B., Casadevall, E., Berkaloff, C., and Coute, A. (1990) Journal of Phycology 26, 258-266.
Okada, S., Murakami, M., and Yamaguchi, K. (1995) Journal of Applied Phycology 7, 555-559.
Metzger, P., Casadevall, E., and Coute, A. (1988) Phytochemistry 27, 1383-1388.
Huang, Z., and Poulter, C. D. (1989) Phytochemistry 28, 1467-1470.
Metzger, P., Berkaloff, C., Casadevall, E., and Coute, A. (1985) Phytochemistry 24, 2305-2312.
Weiss, T. L., Chun, H. J., Okada, S., Vitha, S., Holzenburg, A., Laane, J., and Devarenne, T. P. (2010) Journal of Biological Chemistry 285, 32458-32466.
Metzger, P., Rager, M. N., and Largeau, C. (2007) Organic Geochemistry 38, 566-581.
Metzger, P. (1999) Tetrahedron 55, 167-176.
Metzger, P., Rager, M. N., and Largeau, C. (2002) Phytochemistry 59, 839-843.
Okada, S., Tonegawa, I., Matsuda, H., Murakami, M., and Yamaguchi, K. (1997) Tetrahedron 53, 11307-11316.
Niehaus, T. D., Okada, S., Devarenne, T. P., Watt, D. S., Sviripa, V., and Chappell, J. (2011) Proceedings of the National Academy of Sciences of the United States of America 108, 12260-12265.
Okada, S., Devarenne, T. P., and Chappell, J. (2000) Archives of Biochemistry and Biophysics 373, 307-317.
Achitouv, E., Metzger, P., Rager, M. N., and Largeau, C. (2004) Phytochemistry 65, 3159-3165.
Ueki, N., Matsunaga, S., Inouye, I., and Hallmann, A. (2010) Bmc Biology 8.
Morrison, R. T., and Boyd, R. N. (1973). In Organic Chemistry 3rd edition, Allyn and Bacon, Boston, MA. pp. 109-110.
Hillen, L. W., Pollard, G., Wake, L. V., and White, N. (1982) Biotechnology and Bioengineering 24, 193-205.
Song, L. S. (2003) Analytical Biochemistry 317, 180-185.
Takahashi, S., Yeo, Y., Greenhagen, B. T., McMullin, T., Song, L., Maurina-Brunker, J., . . . Chappell, J. (2007) Biotechnology and Bioengineering 97, 170-181.
Huang, Z., and Poulter, C. D. (1989) Phytochemistry 28, 3043-3046.
Metzger, P., Casadevall, E., Pouet, M. J., and Pouet, Y. (1985) Phytochemistry 24, 2995-3002.
Pompon, D., Louerat, B., Bronine, A., and Urban, P. (1996) Cytochrome P450, Pt B 272, 51-64.
Carland, F., Fujioka, S., and Nelson, T. (2010) Plant Physiology 153, 741-756.
Merchant, S. S., Prochnik, S. E., Vallon, O., Harris, E. H., Karpowicz, S. J., Witman, G. B., . . . Team, J. G. I. A. (2007) Science 318, 245-251.
Niehaus, T, Kinison, S., Okada, S., Civ, P., DeVareene, T., Chappell, J. (2012) J. Biol. Chem. 287(11): 8163-73.

* cited by examiner

*Primary Examiner* — Maryam Monshipouri
(74) *Attorney, Agent, or Firm* — Stites & Harbison PLLC; Stephen J. Weyer; Mandy Wilson Decker

(57) ABSTRACT

A method and system are provided for the production of triterpene including methylated triterpenes. The method and system include isolated nucleic acid sequences encoding triterpene methyltransferases such as triterpene methyltransferases 1, 2, 3. Advantageously, the method and system includes transgenic plant cells via an expression vector for triterpene methyltransferase and optionally various triterpene synthase and prenyltransferase all with tags directing these enzymes to the chloroplast of the transgenic plant cells for using the chloroplast methyl erythritol phosphate (MEP) pathway in the triterpene biogenesis.

25 Claims, 10 Drawing Sheets

PRIOR ART

METHOD AND SYSTEM FOR PRODUCING TRITERPENES

CROSS-REFERENCE TO RELATED APPLICATION

This application claims the benefit of U.S. Provisional Application Ser. No. 61/711,654, filed Oct. 9, 2012, herein incorporated by reference.

FIELD OF THE INVENTION

The presently-disclosed subject matter relates to methods and systems for producing triterpenes, and in particular to methods and systems for producing triterpenes, including methylated triterpenes, using expression vectors, isolated gene sequences and genetically engineered, i.e. transgenic organisms, including yeast and plants, which can be used for the production of triterpenes.

BACKGROUND OF THE INVENTION

Triterpenes are terpenes consisting of six isoprene units having a molecular formula $C_{30}H_{48}$. Animals, plants and fungi (e.g. yeast), create triterpenes such as squalene and botryococcene. In recent years, studies have been conducted exploring the uses of triterpenes as biofuels and petroleum chemicals.

Triterpenes may be methylated, for example in the form of mono- and di-methylated forms including mono- and di-methylated forms of squalene and botryococcene to name two, as well as other triterpenes. In nature, for example, animal, plant and fungi, triterpenes metabolism occurs in the cytoplasm utilizing the mevalonate (MVA) pathway. FIG. 1 is a schematic showing typical triterpene metabolism occurring in the cytoplasm of animal plant and fungi cells (left portion, FIG. 1). In nature, and in particular in plant cells having chloroplast, monoterpenes and diterpenes are produced in chloroplasts using the methyl erythrithol phosphate (MEP) pathway, for example as shown in the right side of FIG. 1. However, the MEP pathway occurs exclusively in the chloroplast compartment and is responsible for monoterpene, diterpene and polyterpene (carotenoids and phytol) biosynthesis but not triterpene biosynthesis.

*Botryococcus braunii* accumulates very high levels of methylated triterpenes, compounds that contribute to the buoyancy of the algae and serve as high-valued feedstocks for the petrochemical and chemical industries. Three SAM-dependent methyltransferases catalyzing successive and regio-specific methylations of either squalene or botryococcene are identified. Methylation of the triterpene analogs squalene and botryococcene requires distinct methyltransferases. The observed substrate selectivity and successive cycles of regio-specific catalysis by triterpene methyltransferases from *Botryococcus braunii* provides evidence that further chemical diversification is achievable.

*Botryococcus braunii* is a colony-forming, freshwater green algae reported to accumulate 30 to 86% of its dry weight as hydrocarbon oils (1) Three distinct races of *B. braunii* have been described based on the types of hydrocarbons that each accumulates (2) Race A accumulates fatty acid-derived alkadienes and alkatrienes (3), race L accumulates the tetraterpene lycopadiene (4), and race B accumulates triterpenes, predominately botryococcene, squalene and their methylated derivatives (5) The oils accumulate both in intracellular oil bodies and in association with an extracellular matrix (6), which in race B consists largely of long-chain, cross-linked biopolymers formed in part from acetalization of polymethylsqualene diols (7) Di- and tetra-methylated botryococcenes are generally the most abundant triterpenes accumulating in race B with smaller amounts of tetramethylated-squalene (8) and other structural derivatives of squalene and botryococcene that range from C31 to C37 accumulating to various levels in different strains and in response to variable culture conditions (9) Other polymethylated derivatives such as diepoxy-tetramethylsqualene (10), botryolins (11), and brauixanthins (12) have also been reported.

*B. braunii* race B has received significant attention because it is considered an ancient algal species dating back at least 500 MYA and is one of the few organisms known to have directly contributed to the existing oil and coal shale deposits found on Earth (13-15), accounting for up to 1.4% of the total hydrocarbon content in oil shales (16) Secondly, because the hydrocarbon oils of *B. braunii* race B are readily converted to starting materials for industrial chemical manufacturing and high quality fuels under standard hydrocracking/distillation conditions in yields approaching 97% (17), race B has been considered a potential production host for renewable petrochemicals and biofuels. However, the slow growth habit of *B. braunii* poses serious limitations to its suitability as a robust biofuel production system.

*B. braunii* race B accumulates triterpene oils in excess of 30% of its dry weight. The composition of the triterpene oils is dominated by di-methylated to tetra-methylated forms of botryococcene and squalene. While unusual mechanisms for the biosynthesis of the botryococcene and squalene were recently described, the enzyme(s) responsible for decorating these triterpene scaffolds with methyl substituents were unknown. A transcriptome of *B. braunii* was screened computationally assuming that the triterpene methyltransferases (TMTs) might resemble the SAM-dependent enzymes described for methylating the side chain of sterols. Six sterol methyltransferase-like genes were isolated and functionally characterized. Three of these genes when co-expressed in yeast with complementary squalene synthase or botryococcene synthase expression cassettes resulted in the accumulation of mono- and di-methylated forms of both triterpene scaffolds. Surprisingly, TMT-1 and TMT-2 exhibited preference for squalene as the methyl acceptor substrate, while TMT-3 showed a preference for botryococcene as its methyl acceptor substrate. These in vivo preferences were confirmed with in vitro assays utilizing microsomal preparations from yeast over-expressing the respective genes, which encode for membrane associated enzymes. Structural examination of the in vivo yeast generated mono- and di-methylated products by NMR identified terminal carbons, C3 and C22/C20, as the atomic acceptor sites for the methyl additions to squalene and botryococcene, respectively. These sites were identical to those previously reported for the triterpenes extracted from the algae themselves. The availability of closely related triterpene methyltransferases exhibiting distinct substrate specificities and successive catalytic activities provides an important tool for investigating the molecular mechanisms responsible for the specificities exhibited by these unique enzymes.

As previously noted, *B. braunii* has attracted considerable interest because it reportedly accumulates hydrocarbon oils from 30 to 86% (1) of its dry weight and because these oils are considered progenitors to oil and coal shale deposits (2-4). While all *B. braunii* are morphologically similar, three distinct chemotypes of *B. braunii* have been reported depending on the type of hydrocarbons each accumulates (5). Race A accumulates fatty acid-derived alkadienes and alkatrienes (6); race L accumulates the tetraterpene lycopadiene (7); and race B amasses the linear triterpenes, botryococcene, squalene, and their methylated derivatives (8). Di- and tetra-methylated botryococcenes are generally the most abundant oils accumulating in race B (9). However, lower amounts of tetramethylated-squalene (10) and variable amounts of other structural derivatives of botryococcene ranging from C31 to C37 accumulate to various levels in different race B strains and in response to variable culture conditions (9,11). The oils accumulate both in intracellular oil bodies and in association with an extracellular matrix (12), which in race B consists mainly of long-chain, cross-linked polyacetals formed in large part from acetalization of polymethylsqualene diols that account for approximately 10% of the dry weight (13). Other polymethylsqualene derivatives have been described in race B, such as diepoxy-tetramethylsqualene (14), botryolins (15), and braunixanthins (16). The linear triterpenes, botryococcene, squalene, and their methylated derivatives, are hence common components of B. braunii race B and make up a large proportion of its total biomass.

A unique mechanism for botryococcene biosynthesis was recently described by Niehaus et al. (17), in which two squalene synthase-like (SSL) enzymes perform the successive half-reactions that are normally catalyzed by a single enzyme in the case of squalene synthase. SSL-1 uses farnesyl diphosphate (FPP) as a substrate to catalyze the production of pre-squalene diphosphate (PSPP), which a second enzyme, SSL-3, converts to botryococcene in an NADPH-dependent manner. A third enzyme, SSL-2, catalyzes the biosynthesis of squalene from PSPP produced by SSL-1 but cannot efficiently use FPP as a substrate. Overall, it was suggested that the squalene and botryococcene produced by the SSL enzymes were channeled into the production of the liquid oils and the biosynthesis of squalene derivatives, such as the extracellular matrix (17), while the conventional B. braunii squalene synthase (18) appears to synthesize squalene destined for sterol biosynthesis.

It is not botryococcene and squalene, however, that accumulate to substantial levels in this algae, but the methylated forms of these triterpenes. For instance, while the liquid oil content of B. braunii race B is composed primarily of botryococcenes, generally less than 1% is in the non-methylated C30 form and the majority is dominated by di-methylated and tetramethylated forms, depending on the strain and culture conditions (9, Metzger, 1983 #102,11). Essentially all the squalene that accumulates is in methylated forms, accumulating in the oil fraction (less than 5% of the total oil (19) or incorporated into a variety of other B. braunii natural products (13-16). Because B. braunii race B accumulates 30% or more of its dry weight as these triterpene components, one can estimate that the methylated triterpenes can account for up to 25% of the total algal biomass dry weight and contribute directly to the buoyancy that distinguishes these algal colonies. Unlike many green algae that are flagellated and phototaxic (20), the buoyance characteristic of Botryococcus provides a means for it to float in its normal aqueous habitats and to intercept a greater amount of photosynthetic light. In addition to these purported physiological roles, the methylated forms of botryococcene and squalene enhance their utility as feedstocks for petrochemical processing and chemical manufacturing. The increased branching evident in the methylated triterpenes improves their hydrocracking to chemical species of value for the synthesis of industrial polymers and other commodity based chemicals (21) and yields high quality gasoline, kerosene and diesel fuels upon distillation (22).

While the unique mechanisms for C30 botryococcene and squalene biosynthesis in Botryococcus braunii have been elucidated (17), the specific mechanism(s) by which these triterpenes are methylated was unclear at the start of this work. Small molecule methylation has been extensively characterized for many diverse compounds and typically consists of a methyltransferase (MT) that utilizes the universal methyl-donor S-adenosyl methionine (SAM), and exhibits variable degrees of selectivity for a wide range of methyl acceptor molecules (24). MTs are also distinguished as C-, O-, N-, S- or halide methyltransferases, an indication of the methylation target within the acceptor substrate. While MTs may only share limited overall amino acid sequence similarities, domains responsible for SAM binding appear to be broadly conserved and highly conserved structural folds have served to associate MTs into five distinct Classes. Most of the small molecule MTs fall into Class 1, but do not appear to cluster phylogenetically based on their target site (i.e. methylation of carbon versus nitrogen) or the particular chemical class of the methyl acceptor substrate. An indole alkaloid MT, for instance, shows closer sequence similarity to a tocopherol MT rather than any other alkaloid specific MTs. Clustering in this instance appears more related to the evolutionary origins of the MTs and the propensity of MTs to undergo neofunctionalization. There remains a need in the art to harness the unique oil biosynthesis capacity for use in a system that allows for rapid and higher yield production.

There remains a need in the art to harness this unique oil biosynthetic capacity for use in a system that allows for more rapid and higher yield production.

SUMMARY OF THE INVENTION

The presently-disclosed subject matter meets some or all of the above-identified needs, as will be evident to those of ordinary skill in the art after a study of information provided in this document.

This disclosure describes several embodiments of the presently-disclosed subject matter, and in many cases lists variations and permutations of these embodiments. Accordingly, this disclosure is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this disclosure does not list or suggest all possible combinations of such features.

The presently-disclosed subject matter relates to triterpene production, including methylated triterpene production. In various forms, the subject matter relates to isolated nucleic acid sequences which encode various proteins including enzymes for the production of triterpenes and including methylated e.g. mono and di-methlyated triterpenes. The presently-disclosed subject matter includes isolated nucleic acids encoding triterpene methyltransferases, genetically modified or engineered triterpene methyltransferase having a chloroplast tag directing the triterpene methyltransferase to chloroplasts of plant cells when the protein is expressed in plant cells, expression vectors expressing a nucleic acid encoding triterpene methyltransferases, genetically modified cells, e.g. plant cells having an expression vector encoding one or more triterpene methyltransferases and methods for transforming cells with an expression vector encoding triterpene methyltransferases.

In addition, the presently-disclosed subject matter is directed to exploiting the MEP pathway of plant cells to produce triterpenes and in particular methylated triterpenes. Using isolated nucleic acids, e.g. expression vectors with nucleic acid sequences encoding specific enzymes which target the products of the MEP pathway in chloroplast, methylated triterpenes are produced. For example, plant cells can be genetically modified to express various triterpene methyltransferases along with triterpene synthases (e.g. squalene synthase and/or botryococcene synthase and prenyltransferase (PT)), all with addressing information (e.g. tags) such that the encoded enzymes are directed to the chloroplast compartment of the transfected plant cells. As a result, the presently engineered mechanism provides a unique metabolism incorporated in a non-native environment within plant cells. From the present design, triterpene biosynthesis can occur in the chloroplast compartment in a manner such that carbon from the MEP pathway can be diverted to triterpene biosynthesis. An advantage of this scheme or approach is to eliminate regulatory mechanisms controlling triterpene biosynthesis which occurs in the cytoplasm and hence the present scheme provides a robust production level of triterpenes. In various alternative forms, the triterpene synthase can include one or more combinations of synthases other than squalene and botryococcene synthases.

The present invention, in one form thereof, relates to an isolated nucleic acid having a nucleic acid sequence encoding at least one protein selected from the group consisting of triterpene methyltransferase 1 (TMT-1), triterpene methyltransferase 2 (TMT-2) and triterpene methyltransferase 3 (TMT-3). In one further embodiment, the nucleic acid sequence encodes at least two proteins selected from the group consisting of TMT-1, TMT-2 and TMT-3 or alternatively all three proteins. The nucleic acid sequence may be selected from the group consisting of SEQ ID NOS: 1, 2 and 3.

In one advantageous form, the isolated nucleic acid may include non-native nucleic acid sequences of TMT-1, TMT-2 and TMT-3. As used throughout this disclosure, non-native nucleic acid sequences include nucleic acids sequences which are not found in the native forms of the nucleic acid sequences, i.e. sequences that are not found in nature or naturally occurring with genes for encoding triterpene methyltransferases. These non-native (to triterpene methyltransferases) nucleic acid sequences may occur at the 5' end, 3' end or within the sequence of the nucleic acid sequences encoding TMT-1, TMT-2 and TMT-3.

In yet another alternative form, the isolated nucleic acid may include a chloroplast target sequence, wherein when the nucleic acid is expressed in a plant cell with chloroplasts, the protein is directed to the chloroplasts.

The present invention, in another form thereof, relates to a non-naturally occurring protein in the form of a triterpene methyltransferase with a chloroplast tag wherein, the triterpene methyltransferase is directed to chloroplasts of plant cells when the protein is synthesized in the plant cells. In various further specific advantageous forms, the triterpene methyltransferase may be TMT-1, TMT-2 and/or TMT-3. The protein may have an amino acid sequence encoded from a nucleic acid having a nucleic acid sequence selected from the group consisting of SEQ ID NOS: 1-3.

The present invention in another form thereof relates to an expression vector comprising a nucleic acid having a nucleic acid sequence encoding a protein selected from the group consisting of triterpene methyltransferase 1, triterpene methyltransferase 2 and triterpene methyltransferase 3. In one further specific form, the expression vector includes a sequence encoding at least one triterpene synthase such as squalene synthase or botryococcene synthase or both. In one form, the triterpene synthases may be from *B. braunii*. In yet a further specific form, the nucleic acid may also have a sequence encoding prenyltransferase.

In yet an alternative, further form, the expression vector may include one or more chloroplast target sequences wherein when the expression vector is used to transform a plant cell and the nucleic acid is expressed in the plant cell, one or more proteins encoded by the expression vector are directed to a chloroplast.

The present invention, in another form thereof, relates to a transfected plant cell with an expression vector comprising a nucleic acid having a nucleic acid sequence encoding a protein selected from the group consisting of triterpene methyltransferase 1, triterpene methyltransferase 2 and triterpene methyltransferase 3. In various further advantageous forms, the expression vector further includes genes for triterpene synthase such as squalene synthase and/or botryococcene synthase. In yet a further form, the nucleic acid further includes a sequence encoding prenyltransferase. In a still further form, one or more of the triterpene methyltransferases, triterpene synthases and prenyltransferase include a sequence targeting these proteins to the chloroplasts of the plant cell.

The present invention, in yet another form thereof relates to a method for transforming a cell which includes transfecting a plant cell with an expression vector comprising a nucleic acid having a nucleic acid sequence encoding one or more protein sequences selected from the group consisting of TMT-1, TMT-2 and TMT-3. In various further form, the expression vector may further include nucleic acid sequences for encoding one or more triterpene synthases and prenyltransferase. Advantageously, the proteins include a tag or address which directs the enzymes to the chloroplast compartment of the transfected plant cell.

The presently-disclosed subject matter relates to methylation of a triterpene analogs of squalene and botryococcene using different methyltransferases.

Further, the present-disclosed subject matter relates to mechanisms for the biosynthesis of botryococcene and squalene analogs using specific enzymes responsible for decorating these triterpene scaffolds with methyl substitutes.

In addition, the present-disclosed subject matter relates to genetically engineered or transgenic yeast and plants which have triterpene methyltransferase (TMTs) which provide methylation of a side chain of sterols.

Further, the present subject matter relates to genetically engineered yeast which has been modified to specifically express methyltransferase-like genes including yeast which have been transformed to co-express complimentary squalene synthase or botryococcene synthase.

In addition, the present subject matter relates to the use of TMT-1 and TMT-2 for methylation of squalene and TMT-3 for the methylation of botryococcene.

BRIEF DESCRIPTION OF THE DRAWINGS

FIG. 4 shows amino acid alignment of six sterol C-24 methyltransferases-like genes from *B. braunii* race B along with those of *C. reinhardtii* (EDP05221) and *A. thaliana* (AAG28462) identified as SEQ ID NOS: 7-14. Conserved sterol-binding domains (SMT) and S-adenosyl methionine-binding domains (SAM) as identified by (27) are boxed and labeled in blue or red, respectively.

DETAILED DESCRIPTION

Figure 1:
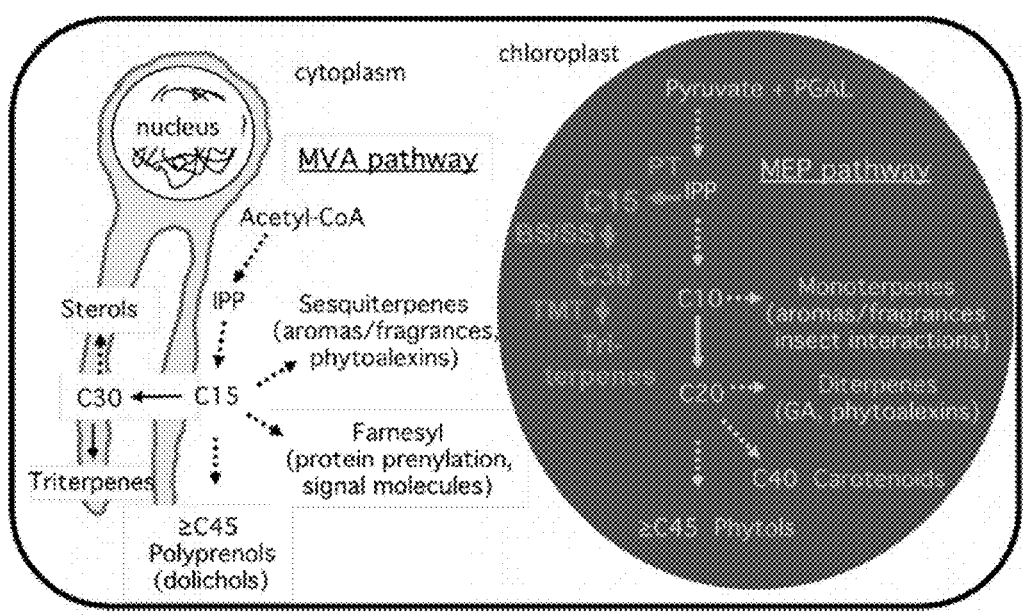
FIG. 1 is a schematic illustrating the mevalonate (MVA) pathway in cytoplasm of wild type cells (left side) and the methyl erythritol phosphate (MEP) pathway of plant chloroplast (right side).

The details of one or more embodiments of the presently-disclosed subject matter are set forth in this disclosure. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Some of the polynucleotide and polypeptide sequences disclosed herein are cross-referenced to GENBANK®/GENPEPT® accession numbers. The sequences cross-referenced in the GENBANK®/GENPEPT® database are expressly incorporated by reference as are equivalent and related sequences present in GENBANK®/GENPEPT® or other public databases. Also expressly incorporated herein by reference are all annotations present in the GENBANK®/GENPEPT® database associated with the sequences disclosed herein. Unless otherwise indicated or apparent, the references to the GENBANK®/GENPEPT® database are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. By way of providing an example, about 60% is inclusive of: 60%±0.1%, which is inclusive of 59.9%-60.1%, and so forth.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises because of degeneracy of the genetic code wherein more than one codon codes for the same amino acid.

It is understood that the addition of sequences that do not alter the encoded activity of a nucleic acid molecule, such as the addition of a non-functional or non-coding sequence, is a conservative variation of the basic nucleic acid molecule. The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants.

One of skill in the art will appreciate that many conservative substitutions of the nucleic acid constructs which are disclosed herein yield a functionally identical construct. For example, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid.

It will be appreciated by those skilled in the art that due to the degeneracy of the genetic code, a multitude of nucleotide sequences encoding modified triterpene synthase polypeptides of the presently-disclosed subject matter may be produced, some of which bear substantial identity to the nucleic acid sequences explicitly disclosed herein. For instance, codons AGA, AGG, CGA, CGC, CGG, and CGU all encode the amino acid arginine. Thus, at every position in the nucleic acid molecules of the presently-disclosed subject matter where an arginine is specified by a codon, the codon can be altered to any of the corresponding codons described above without altering the encoded polypeptide. It is understood that U in an RNA sequence corresponds to T in a DNA sequence.

A polynucleotide, polypeptide, or other component is "isolated" when it is partially or completely separated from components with which it is normally associated (other proteins, nucleic acid molecules, cells, synthetic reagents, etc.). A nucleic acid molecule or polypeptide is "recombinant" when it is artificial or engineered, or derived from an artificial or engineered protein or nucleic acid molecule. For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant. For example, an "isolated" nucleic acid molecule is one which is separated from other nucleic acid molecules which are present in the natural source of the nucleic acid molecule. For example, with regards to genomic DNA, the term "isolated" includes nucleic acid molecules which are separated from the chromosome with which the genomic DNA is naturally associated. Typically, an "isolated" nucleic acid molecule is free of sequences which naturally flank the nucleic acid molecule (i.e., sequences located at the 5' and 3' ends of the nucleic acid molecule) in the genomic DNA of the organism from which the nucleic acid molecule is derived. For example, in various embodiments, the isolated nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid molecule is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

The presently-disclosed invention is based on the conventional beliefs that botryococcene biosynthesis resembles that of squalene, a metabolite essential for sterol metabolism in all eukaryotes. Squalene arises from an initial condensation of two molecules of farnesyl diphosphate (FPP) to form pre-squalene diphosphate (PSPP), which then undergoes a reductive rearrangement to form squalene. In principle, botryococcene could arise from an alternative rearrangement of the pre-squalene intermediate. Because of these proposed similarities, the present inventors believe that a botryococcene synthase would resemble squalene synthase and hence isolated squalene synthase-like genes from *B. braunii* race B. While *B. braunii* does harbor at least one typical squalene synthase, none of the other three squalene synthase-like (SSL) genes encode for botryococcene biosynthesis directly. SSL-1 catalyzes the biosynthesis of PSPP and SSL-2 the biosynthesis of bisfarnesyl ether, while SSL-3 does not appear able to directly utilize FPP as a substrate. However, when combinations of the synthase-like enzymes were mixed together, in vivo and in vitro, robust botryococcene (SSL-1+SSL-3) or squalene biosynthesis (SSL1+SSL-2) was observed. These findings were unexpected because squalene synthase, an ancient and likely progenitor to the other *Botryococcus* triterpene synthases, catalyzes a two-step reaction within a single enzyme unit without intermediate release, yet in *B. braunii*, these activities appear to have separated and evolved inter-dependently for specialized triterpene oil production greater than 500 MYA. Co-expression of the SSL-1 and SSL-3 genes in different configurations, as independent genes, as gene fusions, or targeted to intracellular membranes, also demonstrate the potential for engineering even greater efficiencies of botryococcene biosynthesis.

The present system and method will now be described with regard to various experiments and examples which provide for additional understanding of the present method and system.

Transgenic plants were created using conventional transformation technology in order to produce transgenic plants which produce triterpenes using the MEP pathway in the chloroplast of the plant cells. The transgenic plants successfully express triterpene methyltransferases in combination with appropriate triterpene synthases, producing mono- and di-methylated forms of squalene and botryococcene. As a result, the transgenic plants introduce triterpenes biosynthesis in the chloroplast compartment in a manner such that the carbon from the MEP pathway is diverted to triterpene biosynthesis. Advantageously, this approach eliminates regulatory mechanisms controlling triterpenes biosynthesis in the cytoplasm, hence providing a robust production level of triterpenes. For exemplary purposes, reference is made to FIG. 1, right side depicting the MEP pathway in chloroplast.

The transgenic plants have been transfected by the introduction of genes for prenyltransferase (PT) specific triterpene synthases (e.g. squalene synthase and/or botryococcene synthase) and various triterpene methyltransferases into the nuclear genome of the plant cells along with addressing information such that the encoded enzymes are directed to the chloroplast compartment of the transgenic plants.

The transgenic plants were created using conventional transformation technology. Gene constructs (FIG. 3) were generated, introduced into *Agrobacterium tumefaciens* and sterile leaf explants where then inoculated with the respective *A. tumefaciens* cultures. Because the gene constructs harbor an antibiotic resistance gene, plant cells transformed with the various gene constructs can be selected and regenerated into intact, individual plants to yield independent transgenic plant lines. The respective plant lines are then propagated in a greenhouse and leaf discs of 1.5 cm harvested in order to extract and profile their triterpenes content by GC-MS (as described previous). In brief, the leaf discs are powdered in liquid nitrogen, the powdered tissue extracted with a 2-3 ml hexane per gm powdered tissue, and the hexane extract clarified by passing it over a silica column (0.5 cm by 2 cm). The column flow-through is then evaluated by standard GC-MS as illustrated in FIG. 2.

Figure 2:
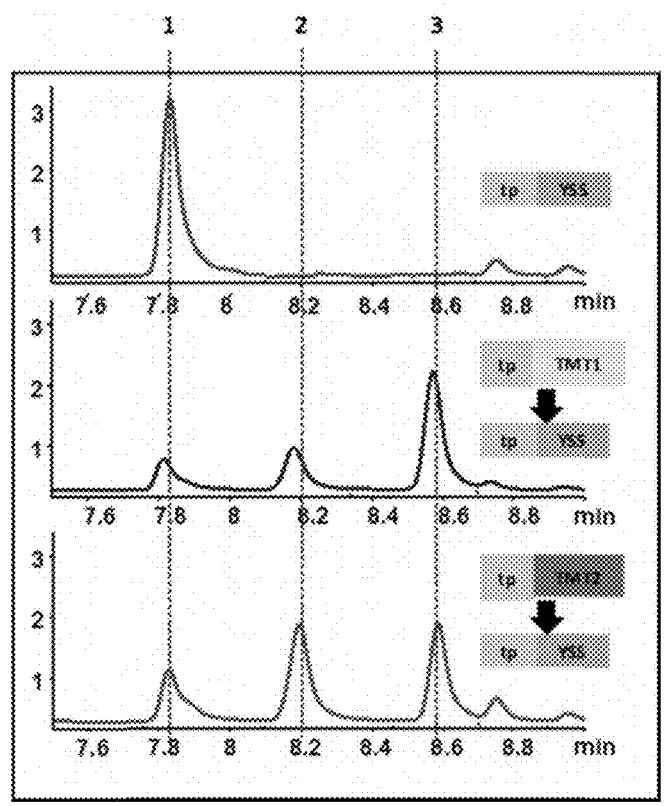
FIG. 2 is a graph showing triterpene content in accordance with the present invention.

FIG. 2 illustrates examples of GC-MS analysis of transgenic plant material for triterpenes content. The upper panel is the analysis of a plant engineered for only squalene production in the chloroplast compartment and was demonstrated to accumulate high levels of squalene (peak #1, verified by authentic standards and MS match). This same transgenic plant line was then engineered separately with a gene encoding for triterpene methyltransferase 1 (TMT-1) or 2 (TMT-2), the transgenic plants harboring all the transgenes regenerated and profiled by GC-MS. The peaks corresponding to peaks 2 and 3 correspond to monomethylated (2) and dimethylated (3) squalene. An analogous strategy was used to create plant lines accumulating botryococcene produced in the chloroplast, and those high accumulating lines were then engineered with triterpene methyltransferases genes 1, 2 and 3. For the botryococcene engineered lines, only those plant harboring the TMT3 gene accumulated mono- and di-methylated forms of botryococcene. In contrast, for the squalene engineered plants, only those subsequently engineered with TMT-1 and 2 accumulated mono- and di-methylated forms of squalene.

Figure 3:
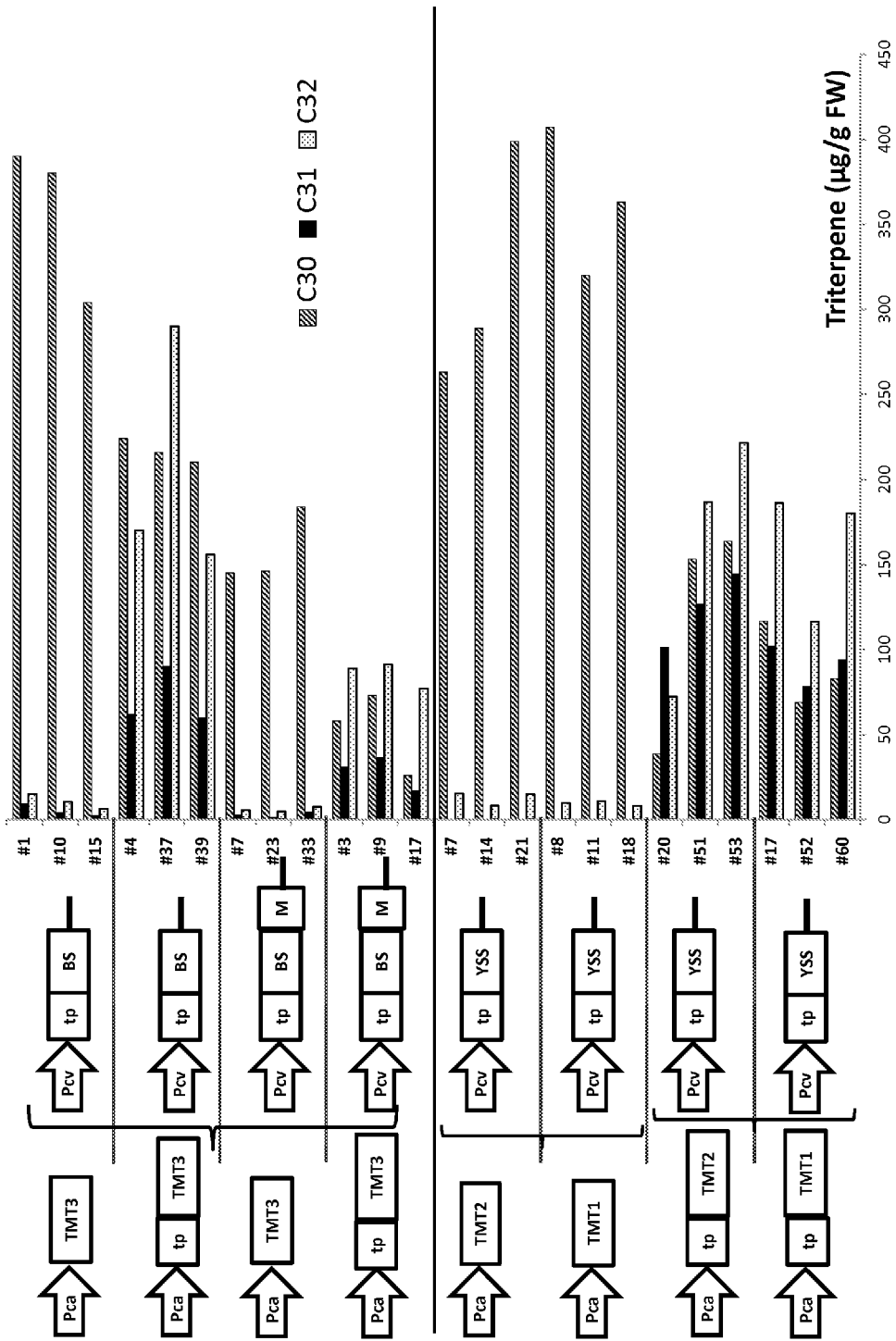
FIG. 3 is chart illustrating triterpene chemical profiles of plants engineered for methylated botryococcene and squalene biosynthesis in accordance with the present invention.

FIG. 3 illustrates the analysis of transgenic plant lines (#) for their triterpenes contents. The upper panel is specific for those plants engineered for botryococcene and methylated botryococcene biosynthesis in the cytoplasm versus the chloroplast compartment. For example, the first three transgenic lines evaluate (#1, 10 and 15) were all engineered for the botryococcene biosynthesis in the chloroplast (as noted by the tp designation), but the triterpene methyltransferase was targeted to the cytoplasm (no tp designation). Expression of both gene constructs were derived by strong constitutive promoter (either the cauliflower mosaic virus 35 S promoter, Pca; or the corresponding cassava mosaic virus promoter, Pcv). The green histogram bars represent the amount of botryococcene accumulation, while the yellow and red bars represent the amount of mono- and di-methylated botryococcene, respectively. Only when both the botryococcene synthase and triterpene methyltransferase are targeted to the chloroplast compartment is there significant triterpenes accumulation and significant amounts of methylated botryococcene observed. The constructs with the botryococcene targeted to the chloroplast compartment and with a carboxy-terminal sequence to direct the BS enzyme to the membrane within the chloroplast (tp-BS-mp), did not yield more botryococcene, but the relative conversion of the botryococcene to its methylated forms was much greater.

FIG. 3 shows an illustration of triterpene chemical profiles of plants engineered for methylated botryococcene and squalene biosynthesis. The lower panel (or half) of FIG. 3 illustrates the same chemical analysis for plants engineered for squalene and methylated squalene production. For example, plants #7, 14, and 21 were engineered for squalene biosynthesis in the chloroplast compartment (tp designation), but triterpenes methyltransferase enzymes 1 and 2 were targeted to the cytosoloic compartment (no tp designation). These plants clearly accumulate high levels of squalene and very little methylated forms. In contrast, when both the squalene synthase and methyltransferase genes are targeted to the chloroplast compartment (tp designations), high levels of mono- and di-methylated forms of squalene accumulate.

It is important to note that only squalene accumulating plants engineered with triterpene methyltransferase 1 and 2, but not TMT-3, accumulate methylated squalene. In contrast, only botryococcene accumulating plants engineered with TMT-3, but not TMT-1 or 2, accumulated methylate botryococcene. This is a demonstration that each methyltransferase exhibits substrate specificity for either squalene or botryococcene.

In an alternative forms or embodiments, transgenic plants are generated using isolated nucleic acid such as expression vectors having nucleic acid sequences encoding various triterpene methyltransferases including ones with tags directing the enzyme(s) to the chloroplast of the transgenic plant cells. Further, the expression vector can include other enzymes for triterpene biosynthesis using the MEP pathway which include one or more triterpene synthases such as squalene synthase or botryococcene synthase and prenyltransferase.

Exemplar Experimental Procedures

The following exemplar experimental procedures provide a better understanding of the presently disclosed subject matter including method and procedures for producing various transgenic cells, isolated nucleic acid sequences and expression vectors for the production of triterpenes.

Cloning the SMT-Like Genes—

The triterpene methyltransferase-3 (TMT-3) identified through a random sequencing effort of ESTs using a *B. braunii* phage cDNA library as previously described (17). Briefly, phages were converted to their plasmid form using the mass excision protocol as described by the manufacturer (Stratagene), and ~500 individual colonies were randomly selected for automated DNA sequencing using sequencing primers flanking the cDNA insertion sites. Manually assembled cDNA sequences were then screened against the NCBI tBlastn search function across all available databases and TMT-3 was identified as exhibiting similarity to C-24-sterol methyltransferase (SMT) genes. All other SMT-like genes were identified in a *B. braunii* 454 transcriptomic dataset as previously described (17). This dataset was screened computationally using a NCBI BLAST search window with the *C. reinhardtii* SMT-1 protein sequence (EDP05221) and the *Arabidopsis thaliana* SMT-1 sequence (AAG28462) as the queries, which led to the identification of six full-length ORFs that were at least 42% identical and 59% similar to *C. reinhardtii* SMT. Full sequence data is available from Genbank. Full sequence data is available from Genbank (TMT-1, JN828962; TMT-2 JN828963; TMT-3, JN828964; SMT-1, JN828965; SMT-2, JN828966; SMT-3, JN828967).

Primers flanked by the BamHI and NotI or EcoRI and NotI restriction enzyme sites were designed to amplify each of the six SMT-like genes from *Botryococcus braunii* mRNA, the amplification products digested with the corresponding restriction enzymes, then ligated into the standard yeast expression vectors YEp352-Ura or pESC-Leu (17). All constructs were verified by DNA sequencing.

Yeast Expression Studies—

Yeast lines previously developed for high level accumulation of squalene and botryococcene were used for evaluating the putative triterpene methyltransferase genes (17,23, 24). These lines consist of the TN7 parental strain harboring an insertional mutation in the native yeast squalene synthase gene (ERG9) transformed with expression vectors containing either the full-length *Botryococcus* squalene synthase (BSS) gene (18) or a fusion of the *Botryococcus* SSL-1 and SSL-3 genes (functional equivalent of botryococcene synthase) including a sequence encoding for the carboxy-terminal membrane targeting domain of the *Botryococcus* squalene synthase protein (SSL-1-3m) (17). The various methyltransferase expression vectors were introduced into these two yeast lines using the lithium acetate transformation protocol, followed by selection for complementation of the uracil and leucine auxotrophic growth markers (24). Transformants were confirmed to possess the various expression vectors using colony PCR with primers selective for the methyltransferase genes. Individual colonies were subsequently grown in 30 ml of the appropriate Yeast Synthetic Drop-out medium (selection) containing 5 mg/l ergosterol for the indicated time at 30° C. before analyzing the cultures for production of novel triterpene components.

In brief, 1 ml aliquots of the culture were combined with 1 ml of acetone, mixed vigorously, and incubated at room temperature for 10 min. One ml of hexane was added and mixed vigorously for 60 sec. The mixture was then centrifuged briefly at 500 g to separate the phases, and an aliquot of the organic phase (1-3 μl) analyzed by GC-MS with a Varian CP-3800 GC coupled to a Varian Saturn 2200 MS/MS (Varian Medical Systems) using a Supelco SLB-5 ms fused silica capillary column (30 m×0.25 mm×0.25 μm film thickness, Supelco). The initial oven temperature was set at 220° C. for 1 min., ramped to 280° C. at 20° C./min., then ramped to 298° C. at 3° C./min.

Purification of Mono- and Di-Methylated Triterpenes—

Yeast lines containing the respective triterpene synthase and TMT expression cassettes were grown in 1 L Yeast Synthetic Drop-out medium media containing 5 mg/l ergosterol at 28° C. for 8 days, after which hexane extracts were prepared. The crude extracts were then subject to HPLC separation on a Waters 2695 HPLC with a Waters 2996 Photodiode Array detector (Waters Corporation) and a Develosil 60-3, 250 mm×20 mm column (Nomura Chemical), run in isocratic mode (100% n-hexane) at 8 ml/min. Under these conditions, C32 botrycooccene, C31 botryococcene, C32 squalene, and C31 squalene eluted at ~18, 22, 32, and 34 minutes, respectively. Repetitive chromatographic runs afforded further purification of the various compounds.

Figure 7:
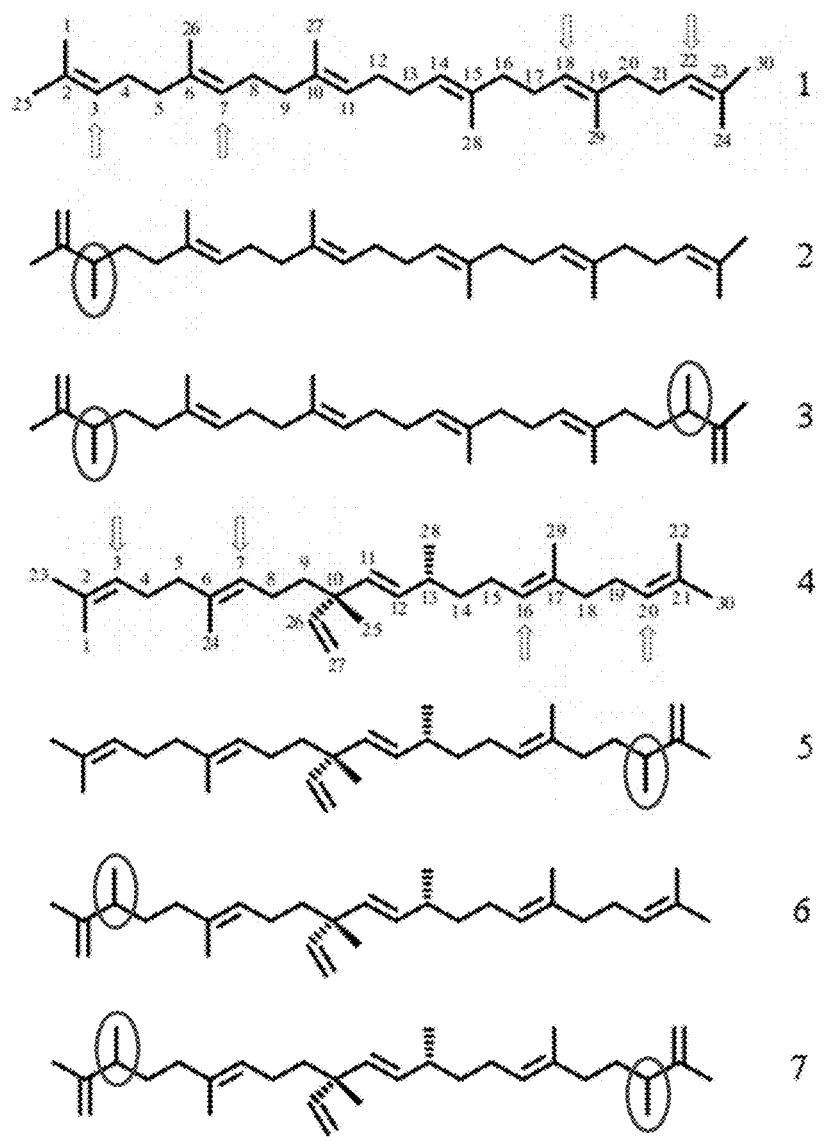
FIG. 7 shows the structures of the various triterpenes (compounds 1-7) accumulating in yeast expressing squalene synthase or botryococcene synthase in combination with TMT-1, -2 or -3 in accordance with the present invention. Yeast expressing the squalene synthase (BSS) gene accumulates squalene (1), and C31 mono-methylated squalene (2) and C32 di-methylated squalene (3) when co-expressed with the TMT-1, TMT-2, or TMT-3 genes. Yeast expressing the botryococcene synthase expression cassette (SSL-1-3m) accumulates C30 botryococcene (4), but a mixture of C31 mono-methylated isomers, showacene (5) and isoshowacene (6), and C32 di-methylated botryococcene (7) when co-expressed with TMT-3. Squalene and botryococcene have their carbons labeled, and the common sites of methylation are indicated with red arrows. The mono- and di-methylation sites with the triterpenes that accumulate in the respective yeast lines are highlighted with red circles. Methylation sites were assigned according to NMR signatures of the isolated compounds (Table S1) with reference to those previous reported (16, 20, 31, 34, 35).

NMR of methylated triterpenes—$^1$H and $^{13}$C NMR spectra were recorded on a JEOL alpha 600 NMR spectrometer at 300K. Chemical shifts were referenced relative to solvent peaks, namely $d_H$ 7.24 and $d_C$ 77.1 for $CDCl_3$. Each product was identified as shown in FIG. 7 by reference to $^{13}$C chemical shifts for botryococcenes and methylsqualenes previously reported (10,16,19,25,26).

In Vitro Assays for the Methyltransferase Activities—

The various *B. braunii* SMT-like genes or empty vector control were expressed in TN-7 yeast and grown in 100 ml selection media for 3 days, after which microsomes were prepared according to the methods of Pompon et al. (27). Enzyme assays contained 50 mM HEPES, pH 7.5, either 0.01% (TMT-3) or 0.1% (all other samples) DHPC, 2 mM acceptor substrate (botryococcene, squalene, C32-botryococcene, C32-squalene, cycloartenol, zymosterol, or lanosterol), 50 μM 3H-SAM (~150 dpm/pmole), 2 μl microsomes, in 100 μl total volume. Assays were set up by first combining everything except 3H-SAM and microsomes and treating with a sonicating water bath (Branson 2510) for ~1 min. until the solution became cloudy due to micelle formation, after which 3H-SAM and microsomes were added and the reaction incubated at 37° C. for 5 min. Reactions were stopped by adding an equal volume of 10% (w/v) KOH in methanol, followed by extraction of hydrocarbon products with 400 μl n-hexane. An aliquot of the organic phase was spotted on silica TLC plates and developed with n-hexane: MTBE (25:1). Triterpenes were visualized with iodine vapor and the corresponding zones were scraped and subject to scintillation analysis.

Results

Figure 4:
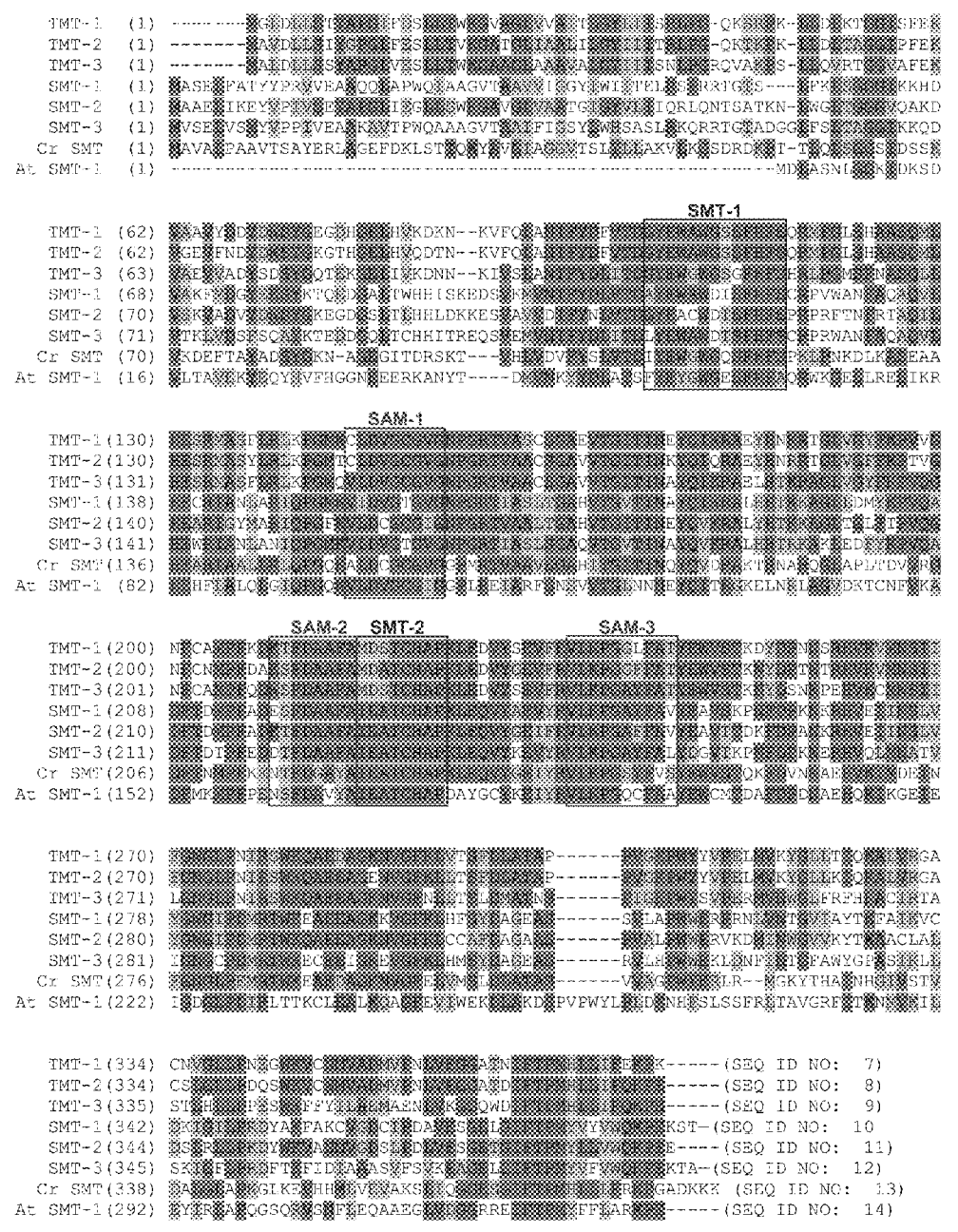

Identification of Triterpene Methyltransferase Candidate Genes— from experiments conducted one predicts that a methyltransferase acting on squalene or botryococcene would resemble a C-24 sterol methyltransferase (SMT) because these enzymes act on the linear isoprenoid side chain of sterols. A *B. braunii* transcriptomic database (17) was screened computationally for cDNAs showing amino acid sequence similarities to the *A. thaliana* and *C. reinhardtii* SMT-1 enzymes. The BLAST search revealed six candidate genes that were greater than 42% identical and 59% similar to the *C. reinhardtii* SMT-1 (FIG. 4). For comparison, the *A. thaliana* genome contains three predicted SMT genes (28), and the *C. reinhardtii* genome contains only one SMT gene (29). These particular genes appear overrepresented in *B. braunii* compared to other plants and algae and enhanced the prospects these could be triterpene methyl-transferases (TMTs). Amino acid alignments revealed that all six candidate genes share three conserved SAM binding sites as identified by Kagen and Clarke (28); however, the sterol binding domain SMT-2, which is invariant in all known plant SMTs (31, 32), is absolutely conserved in three of the candidates (SMT-1, -2, and -3), but not so in the other three (TMT-1, -2, and -3) (FIG. 4). In contrast to other sterol methyltransferases (31, 32), the *B. braunii* MTs possess distinct amino-terminal hydrophobic regions within the first 50 amino acids indicative that these proteins might not behave as soluble proteins but rather might associate with membrane systems.

In Vivo Functional Characterization of MT Activities—

Figure 5:
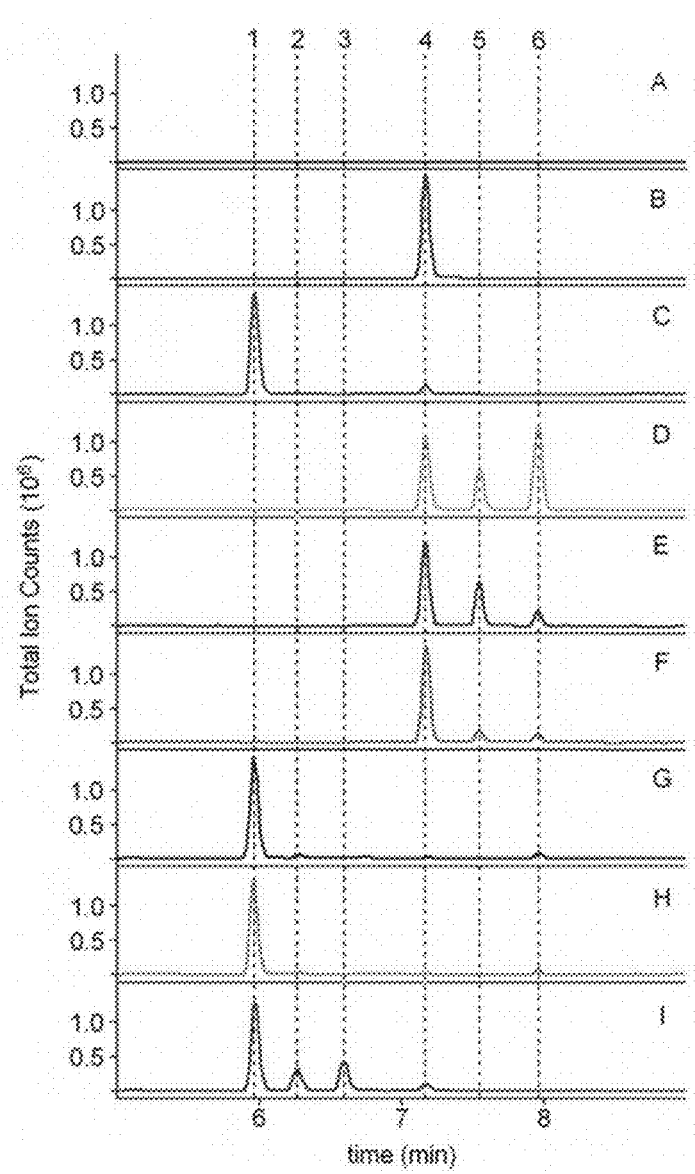
FIG. 5 is a graph providing a functional characterization of *B. braunii* race B TMT genes. Yeast expressing various combinations of triterpene synthase and TMTs were grown in shake flask for five days and organic extracts analyzed by GC-MS (chromatograms shown). TMT genes were co-expressed with BSS (squalene synthase) [TMT-1 (D), TMT-2 (E), and TMT-3 (F)], or SSL-1-3m (botryococcene synthase) [TMT-1 (G), TMT-2 (H), and TMT-3 (I)]. Yeast expressing only BSS (B) or SSL-1-3m (C) or only harboring empty expression vectors (A) serve as background controls. The chromatograms are annotated for the elution behavior of C30-botryococcene (1), C31-botryococcene (2), C32-botryococcene (3), squalene (4), C31-squalene (5), and C32-squalene (6).
Figure 9:
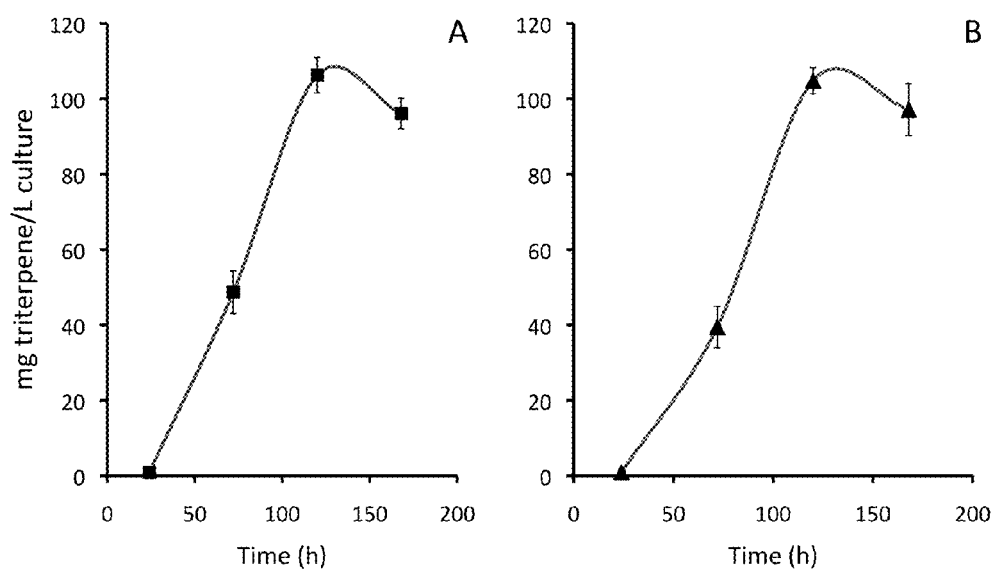
FIG. 9 comprises two graphs in panels (A) and (B) showing the accumulation of triterpenes in yeast engineered with various triterpene synthases in accordance with the present invention. Yeast line TN-7 was engineered with either *B. braunii* squalene synthase (panel A, left side) or SSL-1-3m (panel B, right side) and accumulation of squalene (squares), or botryococcene (triangles) measured. Yeast were grown in selection media in shake flasks at 30° C. for the indicated time and organic extracts analyzed by GC-MS. Data represents mean±S.E.M.

To screen the six candidates for TMT capabilities, we co-expressed the various SMT-like genes in TN7 yeast engineered with either *B. braunii* squalene synthase (BSS) or a construct in which SSL-1 and SSL-3 are fused with a (GSGG)3 amino acid linker and also contains the 73 C-terminal amino acids of BSS fused to its C-terminus (SSL-1-3m). TN7 yeast engineered with BSS or SSL-1-3m can accumulate squalene or botryococcene, respectively, to levels above 100 mg/L (FIG. 5 (row B, row C) and FIG. 9). When SMT-1, -2, or -3 were co-expressed with either BSS or SSL-1-3m, no distinct products could be detected in organic extracts by GC-MS analysis (data not shown); however, co-expression of TMT-1, -2, or -3 all resulted in the accumulation of several unique products (FIG. 5, rows D-I). Analysis of the mass spectra of the unique peaks showed parent ions of 424 and 438 amu (FIG. 10), suggesting mono- and di-methylated triterpenes, respectively.

Figure 6:
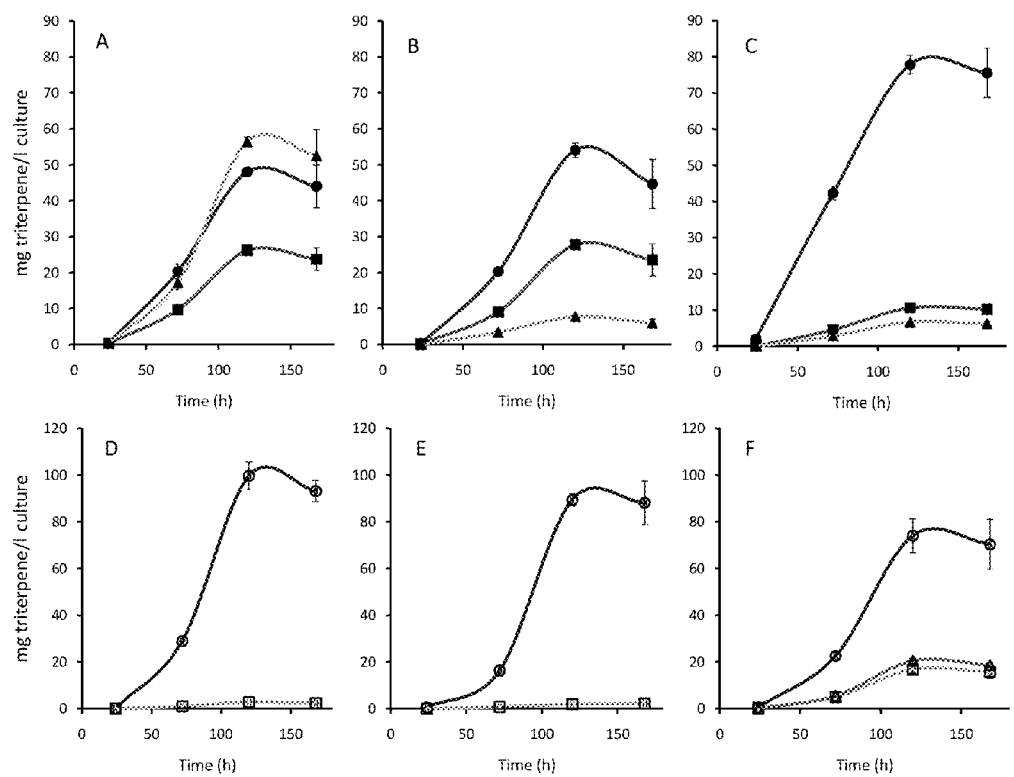
FIG. 6 consists of graphs (A)-(F) showing accumulation of triterpenes in yeast engineered with various triterpene synthases and triterpene methyltransferases (TMT's). Yeast were engineered with *B. braunii* squalene synthase (BSS) and either TMT-1 (A), TMT-2 (B), or TMT-3 (C) on separate plasmids and accumulation of squalene (closed circles), C31 squalene (closed squares), and C32 squalene (closed triangles) measured, or with the botryococcene SSL-1-3m and either TMT-1 (D), TMT-2 (E), or TMT-3 (F) on separate plasmids and accumulation of C30 botryococcene (open circles), C31 botryococcene (open squares), and C32 botryococcene (open triangles) measured. Yeast was grown in shake flasks at 30° C. for the indicated time and organic extracts analyzed by GC-MS. Data represents mean±S.E.M of 3 replicates.

When TMT-1 was co-expressed with BSS, 63% of the total squalenes accumulated as methyl-derivatives with 43% accumulating as dimethyl-squalene (FIG. 5, row D, FIG. 6, panel (A)). However, when coexpressed with SSL-1-3m, only 3% of the total botryococcenes accumulated as monomethyl-botryococcene and no dimethyl-botryococcene was detected (FIG. 5, row G, and FIG. 6, panel (D)). Similarly, when TMT-2 was co-expressed with BSS, 40% of squalenes accumulated as methyl-derivatives with 31% accumulating as monomethyl-squalene (FIG. 5, row E, and FIG. 6, panel (B)). Only 2% of total botryococcenes accumulated as monomethyl-botryococcene when co-expressed with SSL-1-3m (FIG. 5, row H and FIG. 6, panel (E)). When TMT-3 was co-expressed with BSS, approximately 18% of the total accumulating squalene was converted to its methyl-derivatives, with 11% of that as monomethyl-squalene (FIG. 5, row F and FIG. 6, panel (C)). When TMT-3 was co-expressed with SSL-1-3m, 33% of the accumulating botryococcene was methylated with greater than half of that in the dimethyl-botryococcene form (FIG. 5, row I and FIG. 6, panel (F)).

While the conversion of botryococcene and squalene to their mono- and di-methyl derivatives were readily detected, no further methylated products (tri- and tetra-methylated) accumulated. In view of the forgoing it was believed that multiple methyltransferases might act successively and cooperatively in the formation of C34 triterpenes, with one methyltransferase catalyzing the C30 to C32 conversion and another using C32 as a substrate to form a C34 triterpene. To test this possibility, yeast expressing either BSS or SSL-1-3m with TMT-1, TMT-2 or TMT-3 as well as one of the remaining five other SMT-like *B. braunii* genes were evaluated for their triterpene content. No unique products other than the C31 and C32 triterpenes observed in the yeast lines expressing only TMT-1, -2 or -3 (FIG. 5) were detected by GC-MS analysis (data not shown).

In Vitro Biochemical Confirmation—

To verify the in vivo results with in vitro determinations, the six SMT-like genes were expressed in yeast and microsomal preparations used as the source of the enzymes in assays containing 3H-SAM and either botryococcene or squalene as substrates. TMT-1 and TMT-2 readily catalyzed the transfer of a methyl group from SAM to squalene, but showed less than $\frac{1}{100}$ of those levels of activity with botryococcene as the acceptor (See Table 1)

TABLE 1

Substrate preference of the various *B. braunii* SMT-like enzymes[a]

| substrate | empty | TMT-1 | TMT-2 | TMT-3 | SMT-1 | SMT-2 | SMT-3 |
|---|---|---|---|---|---|---|---|
| squalene | 0 | 513.7 ± 8.6 | 862.2 ± 59.9 | 35.4 ± 3.0 | 0 | 0 | 0 |
| botryococcene | 0 | 3.3 ± 1.3 | 4.5 ± 1.3 | 434.9 ± 31.8 | 0 | 0 | 0 |
| $C_{32}$ squalene | 0 | 0 | 0 | 0 | 0 | 0 | 0 |
| $C_{32}$ botryococcene | 0 | 0 | 0 | 0 | 0 | 0 | 0 |

Enzyme activity (pmoles/h/μg)

[a]The various *B. braunii* SMT-like genes or empty vector control were constitutively expressed in yeast for 3 days, after which microsomes were prepared according to the methods of Pompon et al. (36). Enzyme assays contained 50 mM HEPES, pH 7.5, either 0.01% (TMT-3) or 0.1% (all other samples) DHPC, 2 mM acceptor substrate (botryococcene, squalene, $C_{32}$ botryococcene, $C_{32}$ squalene), 50 μM $^3$H-SAM (~150 dpm/pmole), 2 μL aliquots of microsomes (~μg protein) in 100 μL final reaction volume. Assays were set up by first combining everything except $^3$H-SAM and microsomes, and sonicating the mixture until the solution became cloudy due to micelle formation. The $^3$H-SAM and microsomes were added, and the reaction incubated at 37° C. for 5 min. Reactions were stopped by adding an equal volume of 10% KOH in methanol, followed by extraction of hydrocarbon products with 400 μL n-hexane. Aliquots of the hexane extract were separated by TLC and radioactivity incorporated into the triterpene fractions determined by scintillation counting. Data is reported as pmoles of methyl groups transferred to acceptor substrate per unit time and per μg of microsomal protein. Data represents mean ± S.E.M., (of 3 replicates, i.e. n = 3)

In contrast, TMT-3 favored botryococcene as the methyl acceptor and exhibited only very modest activity with squalene. None of the other 3 SMT-like genes showed any measurable methyltransferase activity with botryococcene or squalene as substrates. None of the six enzymes was able to methylate C32 botryococcene or C32 squalene, possible intermediates to the tetramethylated forms (see below). Equally surprising, none of the six *B. braunii* SMT-like genes methylated cycloartenol, zymosterol, or lanosterol (data not shown), which suggested a proper substrate(s) for these MTs, that was not located this hydrophobic substrates were not in a form available for catalytic turnover, or that the MTs were not catalytically competent under these in vitro conditions.

Chemical Identification of the Reaction Products—

To determine the specific methylation sites on squalene and botryococcene, the mono- and di-methylated squalenes and botryococcenes produced in vivo by the engineered yeast were purified and subjected to $^1$H and $^{13}$C NMR analyses (see Tables 2-10, below for complete $^{13}$C NMR assignments).

TABLE 2

C31a botryococcene by TMT3

| C position | $^{13}$C($\delta$) |
|---|---|
| 1 | 17.78 |
| 2 | 131.37 |
| 3 | 124.47 |
| 4 | 26.82 |
| 5 | 39.81 |
| 6 | 134.76 |
| 7 | 124.91 |
| 8 | 23.20 |
| 9 | 41.41 |
| 10 | 42.12 |
| 11 | 135.91 |
| 12 | 133.82 |
| 13 | 36.84 |
| 14 | 37.51 |
| 15 | 25.92 |
| 16 | 124.58 |
| 17 | 135.11 |
| 18 | 37.62 |
| 19 | 33.44 |
| 20 | 40.82 |
| 21 | 150.27 |
| 22 | 109.44 |
| 23 | 25.79 |
| 24 | 16.00 |
| 25 | 23.63 |
| 26 | 146.85 |
| 27 | 111.20 |
| 28 | 21.23 |
| 29 | 16.07 |
| 30 | 19.06 |
| 31 | 19.76 |

TABLE 3

C31b botryococcene by TMT3

| C position | $^{13}$C($\delta$) |
|---|---|
| 1 | 109.44 |
| 2 | 150.24 |
| 3 | 40.82 |
| 4 | 33.44 |
| 5 | 37.58 |
| 6 | 134.80 |
| 7 | 124.80 |
| 8 | 23.20 |
| 9 | 41.45 |
| 10 | 42.12 |
| 11 | 135.89 |
| 12 | 133.84 |
| 13 | 36.77 |
| 14 | 37.46 |
| 15 | 25.90 |
| 16 | 124.69 |
| 17 | 135.07 |
| 18 | 39.81 |
| 19 | 26.82 |
| 20 | 124.50 |
| 21 | 131.34 |
| 22 | 17.78 |
| 23 | 19.06 |
| 24 | 16.00 |
| 25 | 23.63 |
| 26 | 146.85 |
| 27 | 111.20 |
| 28 | 21.23 |
| 29 | 16.07 |
| 30 | 25.79 |
| 31 | 19.76 |

TABLE 4

C32 botryococcene by TMT3

| C position | $^{13}$C($\delta$) |
|---|---|
| 1 | 109.44 |
| 2 | 150.23 |
| 3 | 40.82 |
| 4 | 33.44 |
| 5 | 37.58 |
| 6 | 135.07 |
| 7 | 124.70 |
| 8 | 23.19 |
| 9 | 41.45 |
| 10 | 42.11 |
| 11 | 135.91 |
| 12 | 133.82 |
| 13 | 36.84 |
| 14 | 37.51 |
| 15 | 25.92 |
| 16 | 124.58 |
| 17 | 135.11 |
| 18 | 37.62 |
| 19 | 33.42 |
| 20 | 40.84 |
| 21 | 150.23 |
| 22 | 109.44 |
| 23 | 19.04 |
| 24 | 16.00 |
| 25 | 23.62 |
| 26 | 146.84 |
| 27 | 111.19 |
| 28 | 21.23 |
| 29 | 16.07 |
| 30 | 19.04 |
| 31 | 19.78 |
| 32 | 19.78 |

TABLE 5

C31 squalene by TMT1

| C position | $^{13}$C($\delta$) |
|---|---|
| 1 | 109.46 |
| 2 | 150.25 |
| 3 | 40.79 |
| 4 | 33.42 |
| 5 | 37.59 |
| 6 | 134.99[a] |
| 7 | 124.49[b] |
| 8 | 26.85 |
| 9 | 39.84 |

TABLE 5-continued

C31 squalene by TMT1

| C position | $^{13}C(\delta)$ |
|---|---|
| 10 | 135.19[a] |
| 11 | 124.40[b] |
| 12 | 28.36 |
| 13 | 28.36 |
| 14 | 124.40[b] |
| 15 | 135.17[a] |
| 16 | 39.81[c] |
| 17 | 26.74[d] |
| 18 | 124.36 |
| 19 | 135.25[a] |
| 20 | 39.81[c] |
| 21 | 26.72[d] |
| 22 | 124.19 |
| 23 | 131.34 |
| 24 | 17.76 |
| 25 | 19.03 |
| 26 | 16.09[e] |
| 27 | 16.12[e] |
| 28 | 16.12[e] |
| 29 | 16.09[e] |
| 30 | 25.79 |
| 31 | 19.76 |

TABLE 6

C32 squalene by TMT1

| C position | $^{13}C(\delta)$ |
|---|---|
| 1 | 109.46 |
| 2 | 150.23 |
| 3 | 40.79 |
| 4 | 33.43 |
| 5 | 37.61 |
| 6 | 135.15[f] |
| 7 | 124.19 |
| 8 | 26.73 |
| 9 | 39.86 |
| 10 | 135.25[f] |
| 11 | 124.41 |
| 12 | 28.37 |
| 13 | 28.37 |
| 14 | 124.41 |
| 15 | 135.25[f] |
| 16 | 39.86 |
| 17 | 26.73 |
| 18 | 124.19 |
| 19 | 135.15[f] |
| 20 | 37.61 |
| 21 | 33.43 |
| 22 | 40.79 |
| 23 | 150.23 |
| 24 | 109.46 |
| 25 | 19.03 |
| 26 | 16.08[g] |
| 27 | 16.12[g] |
| 28 | 16.12[g] |
| 29 | 16.08[g] |
| 30 | 19.03 |
| 31 | 19.78 |
| 32 | 19.78 |

TABLE 7

C31 squalene by TMT2

| C position | $^{13}C(\delta)$ |
|---|---|
| 1 | 109.46 |
| 2 | 150.26 |
| 3 | 40.79 |
| 4 | 33.43 |
| 5 | 37.59 |
| 6 | 134.99[a] |
| 7 | 124.49[b] |
| 8 | 26.85 |
| 9 | 39.84 |
| 10 | 135.19[a] |
| 11 | 124.40[b] |
| 12 | 28.36 |
| 13 | 28.36 |
| 14 | 124.40[b] |
| 15 | 135.17[a] |
| 16 | 39.81[c] |
| 17 | 26.74[d] |
| 18 | 124.36 |
| 19 | 135.25[a] |
| 20 | 39.81[c] |
| 21 | 26.72[d] |
| 22 | 124.19 |
| 23 | 131.34 |
| 24 | 17.76 |
| 25 | 19.03 |
| 26 | 16.08[e] |
| 27 | 16.13[e] |
| 28 | 16.13[e] |
| 29 | 16.08[e] |
| 30 | 25.79 |
| 31 | 19.76 |

TABLE 8

C32 squalene by TMT2

| C position | $^{13}C(\delta)$ |
|---|---|
| 1 | 109.45 |
| 2 | 150.26 |
| 3 | 40.79 |
| 4 | 33.42 |
| 5 | 37.59 |
| 6 | 135.17[f] |
| 7 | 124.18 |
| 8 | 26.71 |
| 9 | 39.86 |
| 10 | 135.25[f] |
| 11 | 124.40 |
| 12 | 28.35 |
| 13 | 28.35 |
| 14 | 124.40 |
| 15 | 135.25[f] |
| 16 | 39.86 |
| 17 | 26.71 |
| 18 | 124.18 |
| 19 | 135.17[f] |
| 20 | 37.59 |
| 21 | 33.42 |
| 22 | 40.79 |
| 23 | 150.26 |
| 24 | 109.45 |
| 25 | 19.04 |
| 26 | 16.08[g] |
| 27 | 16.12[g] |
| 28 | 16.12[g] |
| 29 | 16.08[g] |
| 30 | 19.04 |
| 31 | 19.76 |
| 32 | 19.76 |

TABLE 9

C31 squalene by TMT3

| C position | $^{13}C(\delta)$ |
|---|---|
| 1 | 109.45 |
| 2 | 150.25 |
| 3 | 40.79 |
| 4 | 33.43 |
| 5 | 37.60 |
| 6 | 134.99[a] |
| 7 | 124.49[b] |
| 8 | 26.86 |
| 9 | 39.84 |
| 10 | 135.19[a] |
| 11 | 124.40[b] |
| 12 | 28.36 |
| 13 | 28.36 |
| 14 | 124.40[b] |
| 15 | 135.17[a] |
| 16 | 39.81[c] |
| 17 | 26.75[d] |
| 18 | 124.36 |
| 19 | 135.25[a] |
| 20 | 39.81[c] |
| 21 | 26.72[d] |
| 22 | 124.19 |
| 23 | 131.34 |
| 24 | 17.75 |
| 25 | 19.03 |
| 26 | 16.09[e] |
| 27 | 16.12[e] |
| 28 | 16.12[e] |
| 29 | 16.09[e] |
| 30 | 25.79 |
| 31 | 19.76 |

TABLE 10

C32 squalene by TMT3

| C position | $^{13}C(\delta)$ |
|---|---|
| 1 | 109.46 |
| 2 | 150.25 |
| 3 | 40.79 |
| 4 | 33.42 |
| 5 | 37.60 |
| 6 | 135.16[f] |
| 7 | 124.18 |
| 8 | 26.73 |
| 9 | 39.86 |
| 10 | 135.26[f] |
| 11 | 124.40 |
| 12 | 28.36 |
| 13 | 28.36 |
| 14 | 124.40 |
| 15 | 135.26[f] |
| 16 | 39.86 |
| 17 | 26.73 |
| 18 | 124.18 |
| 19 | 135.16[f] |
| 20 | 37.60 |
| 21 | 33.42 |
| 22 | 40.79 |
| 23 | 150.25 |
| 24 | 109.46 |
| 25 | 19.04 |
| 26 | 16.08[g] |
| 27 | 16.12[g] |
| 28 | 16.12[g] |
| 29 | 16.08[g] |
| 30 | 19.04 |
| 31 | 19.78 |
| 32 | 19.78 |

[a, b, c, d, e, f, g]Signals with the same letter may be interchangeable in a same column.

$^1$H and $^{13}$C NMR spectra were recorded on a JEOL alpha 600 NMR spectrometer at 300K. Chemical shifts were referenced relative to solvent peaks, namely $d_H$ 7.24 and $d_C$ 77.1 for CDCl$_3$. Each product was identified as shown in FIG. 7 by referring $^{13}$C chemical shifts for botryococcenes and methylsqualenes to those previously reported (1-4).
1. Achitouv, E., Metzger, P., Rager, M. N., and Largeau, C. (2004) *Phytochemistry* 65, 3159-3165
2. Huang, Z., and Poulter, C. D. (1989) *Phytochemistry* 28, 1467-1470
3. Huang, Z., and Poulter, C. D. (1989) *Phytochemistry* 28, 3043-3046
4. Okada, S., Tonegawa, I., Matsuda, H., Murakami, M., and Yamaguchi, K. (1997) *Tetrahedron* 53, 11307-11316

Figure 10:
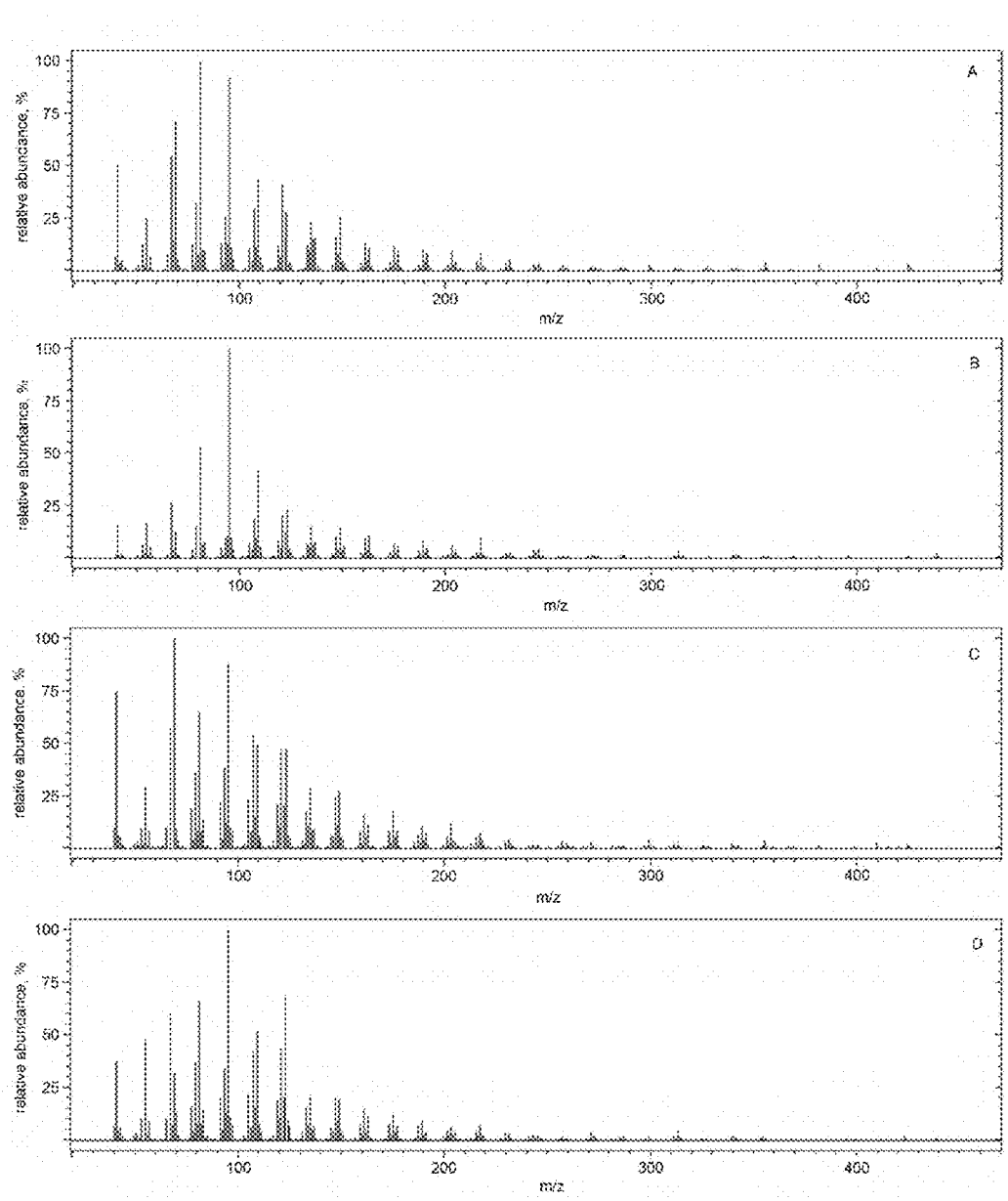
FIG. 10 shows mass spectra of C31 squalene (A) and C32 squalene (B) produced in TN7 yeast expressing BSS and TMT-1, TMT-2 or TMT-3, C31 botryococcene (C) produced in TN7 yeast expressing SSL-1-3m and TMT-1, TMT-2 or TMT-3, and C32 botryococcene (D) produced in TN7 yeast expressing SSL-1-3m and TMT-3.

The mono-methylated squalenes produced by yeast expressing TMT-1, -2, or -3 were all identical based on their NMR signals and methylated at the C-3 position of squalene (FIG. 7, compound 2). Similarly, all the di-methylated squalenes produced by all three yeast lines gave identical NMR signals indicative of methylation at the C-3 and C-22 positions (FIG. 7, compound 3). In contrast, the mono-methylated botryococcene produced by yeast expressing TMT-3 occurred at two positions, either the C-20 position yielding showacene (FIG. 7, compound 5) or the C-3 position yielding isoshowacene (FIG. 7, compound 6). Based on the relative intensity of the NMR signals for the methyl substituent at C-20 in showacene (FIG. 7, compound 5) versus that for C-3 in isoshowacene (FIG. 7, compound 6), showacene accounts for more of the total mono-methylated products than isoshowacene. Di-methylated botryococcene produced by TMT-3 had methyl groups at the C-3 and C-20 positions (FIG. 7, compound 7). The very small amounts of methylated botryococcenes produced in yeast expressing TMT-1 or TMT-2 were not sufficient for NMR analysis; however, the GC-MS patterns of mono-methylated botryococcene produced by TMT-1, -2, and -3 were all identical (FIG. 10). These findings suggest that all the TMT's methylate botryococcene at identical positions.

The large accumulation of triterpene oils by *Botryococcus braunii* race B has provided the impetus for considerable interest in elucidating the biosynthesis of these seemingly simple molecules. The oil is composed largely of linear, branched-chain triterpenes resembling squalene, yet the triterpene scaffold, botryococcene, is synthesized by the successive action of two enzymes rather than a single enzyme like that typical for squalene biosynthesis (17). While small amounts of the C30 botryococcene and squalene triterpenes do accumulate, methylated forms of these molecules predominate and accumulate upwards of 30% of the total algal dry weight. Hence, these algae must possess a robust mechanism(s) for converting the triterpene scaffolds to their methylated forms, that also lend these molecules to a variety industrial applications (23).

Figure 8:
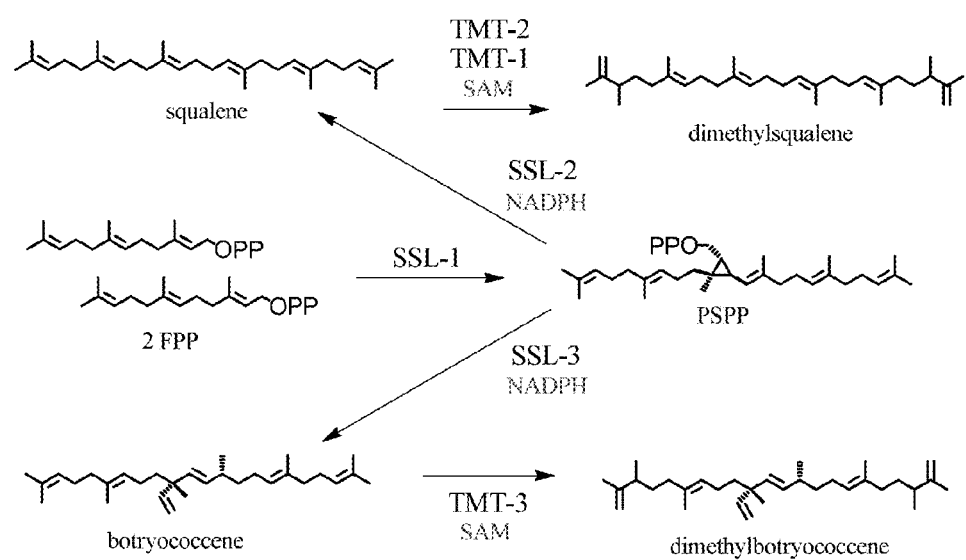
FIG. 8 is a scheme showing the methyl triterpene biosynthetic pathways in *B. braunii*. SSL-1 converts two FPP molecules to PSPP, which is converted in an NADPH-dependent manner to either squalene or C30 botryococcene by SSL-2 or SSL-3, respectively. TMT-1 and TMT-2 can transfer a methyl group from SAM to squalene to form mono- or di-methyl squalene, while TMT-3 acts on C30 botryococcene to form mono- or dimethyl botryococcene.

In the current effort, three triterpene methyltransferases were identified which contribute to the methylation status of botryococcene and squalene, and biochemical properties were uncovered during this investigation. While three-triterpene MTs genes were identified exhibiting sequence similarity to sterol methyltransferases (FIG. 4), two of these encoded enzymes showed activity and specificity for squalene methylation. The third TMT appears to have specificity for botryococcene methylation. The specificity for squalene or botryococcene was unexpected because these molecules have very similar physical features. Nonetheless, the *B. braunii* TMTs were found to discriminate between the two methyl acceptors, as depicted in FIG. 8, and this must arise from the ability of the respective enzymes to recognize differences of the internal linkages within squalene and botryococcene. TMT-3 must be able to recognize the internal ethyl, methyl substituents at C-10 of botryococcene, while TMT-1 and -2 must prefer the straight-chain linkage across C-11, -12, -13 and -14 of squalene.

The substrate specificity of the TMTs was unexpected when one considers the symmetry and asymmetry of squalene, botryococcene and the mono-methylated intermediates, and the successive nature of these catalytic events. Most small molecule MTs catalyze mono-methylation reactions, with some notable exceptions such as the tri-methylation of phosphoethanolamine in the biosynthesis of the choline head group in phospholipid biosynthesis (29). In contrast, the successive methylation of the sterol side-chain at C-24 requires distinct enzymes, sterol methyltransferases 1 and 2 (30, 31). The successive nature of the B. braunii TMTs appears to represent yet another permutation in the activities of this diverse family of enzymes. For TMT-1 and -2, the symmetry of squalene affords equal probability of methylation at either end of the molecule, but these enzymes also introduce a second methylation at the equivalent position on the other side of the molecule. While TMT-1 appears to perform this second methylation with great facility, this is not the case for TMT-2. The accumulation of di-methylated squalene exceeds that for mono-methylated squalene greater than 2-fold in yeast expressing the TMT-1 gene (FIG. 6, panel (A)), but di-methylated squalene only accumulates to approximately 20% of that for mono-methylated squalene in yeast expressing TMT-2 (FIG. 8, panel (B)). TMT-3 functionally resembles TMT-1 with regards to the ease with which it introduces the second methylation into the botryococcene backbone, that is, the accumulation of dimethyl-botryococcene slightly exceeded that of monomethyl-botryococcene (FIG. 8, panel (F)). Based on NMR analysis of the mono-methylated botryococcene produced in yeast, showacene accumulated to higher levels than isoshowacene. It is unclear whether this arises from a preference for methylating botryococcene at C-20 rather than the C-3 position with both monomethylated-botryococcenes serving as equal substrates in the second methylation reaction, or if both the C-3 and C-20 positions of botryococcene are methylated with equal efficiency but isoshowacene (methylated at C-3) is the preferred substrate for the second methylation reaction, or a combination of both possibilities. Regardless, a ratio of showacene to isoshowacene of approximately 1.7 to 1.0 is seen in mono-methylated botryococcene isolated from B. braunii (31), suggesting that yeast expressing TMT-3 and SSL-1-3m recapitulate the same biochemical bias as observed in B. braunii.

The unique specificities of TMT-1, -2 and -3 offer opportunities to gain insights into the biochemical features of these enzymes. Given the large collection of highly conserved the class 1 MT crystal structures and their utility for molecular modeling and mapping residues important for catalysis in the wider family of MT enzymes, a similar strategy might facilitate identifying those regions of these Botryococcus MTs specifying substrate selectivity and target site selection for methylation.

The aforementioned and identified several genes encoding for methyltransferases capable of introducing terminal methyl substituents at C-3 and C-22/C-20 of squalene and botryococcene are provided as examples of some possible enzymes. However, botryococcene and squalene accumulate in B. braunii largely in their tetramethylated forms. Hence, additional MTs or other mechanisms for the complete methylation pattern of these triterpenes are also suitable in accordance with the present disclosure which are readily known or determined using routine experimentation known to one of ordinary skill in the art.

REFERENCES

Numerous references have been cited in this disclosure including the following which are herein incorporated by reference.
1. Brown, A. C., Knights, B. A., and Conway, E. (1969) Phytochemistry 8, 543-547
2. Derenne, S., Largeau, C., Hetenyi, M., BruknerWein, A., Connan, J., and Lugardon, B. (1997) Geochimica Et Cosmochimica Acta 61, 1879-1889
3. Glikson, M., Lindsay, K., and Saxby, J. (1989) Organic Geochemistry 14, 595-&
4. Mastalerz, M., and Hower, J. C. (1996) Organic Geochemistry 24, 301-308
5. Metzger, P., and Largeau, C. (2005) Applied Microbiology and Biotechnology 66, 486-496
6. Gelpi, E., Oro, J., Schneide.H j, and Bennett, E. O. (1968) Science 161, 700-702
7. Metzger, P., Allard, B., Casadevall, E., Berkaloff, C., and Coute, A. (1990) Journal Of Phycology 26, 258-266
8. Okada, S., Murakami, M., and Yamaguchi, K. (1995) Journal Of Applied Phycology 7, 555-559
9. Metzger, P., Casadevall, E., and Coute, A. (1988) Phytochemistry 27, 1383-1388
10. Huang, Z., and Poulter, C. D. (1989) Phytochemistry 28, 1467-1470
11. Metzger, P., Berkaloff, C., Casadevall, E., and Coute, A. (1985) Phytochemistry 24, 2305-2312
12. Weiss, T. L., Chun, H. J., Okada, S., Vitha, S., Holzenburg, A., Laane, J., and Devarenne, T. P. (2010) Journal of Biological Chemistry 285, 32458-32466
13. Metzger, P., Rager, M. N., and Largeau, C. (2007) Organic Geochemistry 38, 566-581
14. Metzger, P. (1999) Tetrahedron 55, 167-176
15. Metzger, P., Rager, M. N., and Largeau, C. (2002) Phytochemistry 59, 839-843
16. Okada, S., Tonegawa, I., Matsuda, H., Murakami, M., and Yamaguchi, K. (1997) Tetrahedron 53, 11307-11316
17. Niehaus, T. D., Okada, S., Devarenne, T. P., Watt, D. S., Sviripa, V., and Chappell, J. (2011) Proceedings of the National Academy of Sciences of the United States of America 108, 12260-12265
18. Okada, S., Devarenne, T. P., and Chappell, J. (2000) Archives Of Biochemistry And Biophysics 373, 307-317
19. Achitouv, E., Metzger, P., Rager, M. N., and Largeau, C. (2004) Phytochemistry 65, 3159-3165
20. Ueki, N., Matsunaga, S., Inouye, I., and Hallmann, A. (2010) Bmc Biology 8
21. Morrison, R. T., and Boyd, R. N. (1973). in Organic Chemistry 3rd edition, Allyn and Bacon, Boston, Mass. pp 109-110
22. Hillen, L. W., Pollard, G., Wake, L. V., and White, N. (1982) Biotechnology And Bioengineering 24, 193-205
23. Song, L. S. (2003) Analytical Biochemistry 317, 180-185
24. Takahashi, S., Yeo, Y., Greenhagen, B. T., McMullin, T., Song, L., Maurina-Brunker, J., . . . Chappell, J. (2007) Biotechnology and Bioengineering 97, 170-181
25. Huang, Z., and Poulter, C. D. (1989) Phytochemistry 28, 3043-3046
26. Metzger, P., Casadevall, E., Pouet, M. J., and Pouet, Y. (1985) Phytochemistry 24, 2995-3002

27. Pompon, D., Louerat, B., Bronine, A., and Urban, P. (1996) *Cytochrome P450, Pt B* 272, 51-64
28. Carland, F., Fujioka, S., and Nelson, T. (2010) *Plant Physiology* 153, 741-756
29. Merchant, S. S., Prochnik, S. E., Vallon, O., Harris, E. H., Karpowicz, S. J., Witman, G. B., . . . Team, J. G. I. A. (2007) *Science* 318, 245-251
30. Niehaus, T, Kinison, S., Okada, S., Civ, P., DeVareene, T., Chappell, J. (2012) J. Biol. Chem. 287(11): 8163-73, including its fifty-one (51) cited references are also herein incorporated by reference.

INCORPORATION BY REFERENCE

All publication, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

```
SEQUENCE LISTING
>Seq1 [Botryococcus braunii race B] triterpene methyltransferase 1 (TMT-1) mRNA,
complete cds
                                                                    (SEQ ID NO: 1)
Atgggattggatctcctttcaacgtacgcccaggcattttgacagtctcctgacttggaagggagtggctggtttggtcgttg ccattaccttgggctacctgatcatatctaggcttcctggacaaaagagccgtccaaagctattggatctaaagacaggag gtatctcctttgagaaggtcgcggccgtgtatgatgactacgacaagtcgtacggggagggagatcacggcgaactgcat gtcaaggacaagaacaaggtcttccaactggctaatactttctacgattttgtaactgatggttacgagtgggcatggggttc gagcttccacttctcccagcgcatgcccggcctgtcccatgcggcttcccagatgctccacgagtcgcgcatggcatcttttt gcgtctgaagccgggaatgaaatgcttggatgtgggctgtggtgtgggcaaccctggacggacagttgcgtcctgcagtg gggccgaggtcaccggcatcaccatcaatgagtaccagatcaagagggcagagtaccacaacaaaggacgggctt ggtgggtacttcaaaccagtggtgggaaatttctgtgccatgccattcaaggataagacttttgatgctgctttcgccatgga ttccacttgccacgcacccaagctggaggacgtgtacagcgaagttttccgtgtcctgaagccaggaggcctgtttgccac atacgagtgggtctccaccaaagactacgaccccaacaactcccgacatgtgaaagtgatgaacagcatcatcttcggc aacggtcttccgaacattcggagctggaaacaggctgaggacgccgggaaaaacgtgggattcaagttggtgacaagc ttcgatctcgccaccgcccccccagttggcaagccctggtactatgtgcccgagctgatggtgaagtatgggctgctgacg attcagaaggctctagtgcgcggagcctgcaacgtgggcctccttcccaatgagggctggaaggtttgcaacatggtcgc cgacatggttcccaaccttgtcgagggtggcgcgacaaacatcttcacccccatgcacttgctcatctttgagaagcccaa gtga >Seq2 [Botryococcus braunii race B] triterpene methyltransferase 1 (TMT-2) mRNA,
complete cds
                                                                    (SEQ ID NO: 2)
Atggcagtagatttgctttcgatctatgggccaggccttttgagagtcttctcacggtaaaaggcgctactggcttgatagctg ctcttatcttaggatacatcataataacaagactgcctggtcaaaagactaaacccaaattactggatttaacagcgggtgg tattccatttgagaaagtcggggaggtgtttaatgattacgacaaatcttatggaaagggaacccacggcgaattgcatgtc caggatacaaataaagtattccaattggcaaacacattttacgactttgtcactgatggttacgagtgggcctggggttcgag cttccacttctcacagcgcatgcctggcttgtctcatgcagcctcgcagatgctccatgaatcacggatggcatcttatctccgt ttgaagccagggatgacatgcttagacgtgggctgtggtgtgggcaacccgggaagaactgtagccgcatgcagtggtg cagttgtgactggaatcactataaacaagtaccagatccaaagggctgagtaccacaacagaaggacgggcttggtgg gattttttaaaccaacagttggaaacttctgcaacatgccatttgatgctaagtcttttgatgccgcttttgcaatggatgccactt gccacgcccccaagctggaagacgtgtatggggaggtcttccgcgtattgaagcctggaggcttctttgctacctatgagtg ggttctacaaagaactatgacccaccaacacgagacatgtcaaagtgatgaacagtatcatctttgggaacggtcttcc gaacataaggagctggaaacaagctgaggaggcaggggagaatgtgggatttaaactgttgacaagttttgaccttgca acagcgcccccagtgggaaagccctggtattatgtgccagagctgatggttaagtatgggcttctaaagatccagaaggc tctggtgcgcggagcctgcagcttgggtcttctccccgaccagagctggaaggtttgcaacatggtcgctgacatggttccc aaccttgtcgagggtggagcaacagacattttcacccctatgcacttgctgatcttccagaagccagaatga
```

-continued

>Seq3 [*Botryococcus braunii* race B] triterpene methyltransferase 1 (TMT-3) mRNA, complete cds (SEQ ID NO: 3)

atggccctggatcttctttcatcctacgctcctggcttggtcgaaagcctgctaacatggaaaggcgcagccggcttggctgc agctgttgccctgggctatattattataagcaaccttcctggaaggcaggttgctaagcccagccttcttcaagtcagaactg gtggcgtcgccttcgagaaggtcgctgaggtagttgccgactacagtgactcttacgggcaaactgaaaagggcgactc atcgtcaaggacaacaacaagattgtctctctcgcgaatactttctatgacctcatcaccgatggatatgagtgggatggg gctccggcttccacttctctcataggctgccaggatgtccttcaatgcatctcagctgctccatgagtcccgtatggcgtctttc ctgcgcctgaagcccggcatgcaagttcttgatgttggctgcggtgtcggaaaccctggcagaacggttgctgcctgcagt ggagcagtggtgactggcatcaccatcaatgcataccagatcaagcgcgctgagttgcacactaagcgggcgggcttgg taggatacttcaagccagttcagggaaacttctgcgcgatgcctttccaagacaagagcttcgatgctgcctttgccatgga ctctacttgccatgcccccaagctggaggtgtgtactccgaggtcttccgcgtgttgaagcctggcgcatactttgcaactta tgagtgggtgtctacaaagaactacgactccaacaacccagagcacgtgaagtgcatgaacagcatcatcctgggcaat ggcctgccgaacatcaggagttggaagcaagctgaggaggcagggaagaacgtgggtttcaacctgcttaccagcctc gacatggctacaaactcccccatcggaaagcctggtactctgtcccagagcgcatggtaaactggggcctgttccgtttc cacaaggcttgcattcgcactgcctctacccctgcatctgctgccgccagaatcctggaagttcttctacatccttgcagagat ggccgagaaccttgtaaagggtgggcaatgggacatcttcaccccatgcacttgctgatcttccaaaagccagagtaa >Seq4 [*Botryococcus braunii* race B] sterol methyltransferase-like 1 (SMT-1) mRNA, complete cds (SEQ ID NO: 4)

atggcgtccgagctcttcgcgacatactaccctcgcgtggtagaggccgctcagcaactcgcaccatggcaaatcgctgc tggagtaaccgcggccgttgttattggtggctatatatggatcatcacagagcttcgtgccctcgacgaacaggaactagt ctgttcaaattgtccggaggtggtattaagaagcacgatgtagcaaaattcatggacggctacgagaaatcatacaaaact caggaagacggtgcgctgacatggcaccacatcagcaaggaggactctgtcqagatggtgaacaccttctacgacctg gtcacagacgcgtatgagtgggcctgggacatctcttttccacttctcctgccgacctgtgtgggccaacttttgcccaggccc aagttctccatgagtgccgcattgccaacctggctcgcatccaacctggcatgaaagttattgatgttggcactggagtggg caaccccggccggaccattgcatcactgacgggggcccatgtgaccggtgtcaccatcaacgcataccagattaagcg ggcgctgcaccacaaagaaggctggcctgttggacatgtacaaaccagtgcaggctgatttcaccgacatgccttttcg ccgacgagagttttgatgctgccttcgcaatgaagccacctgccacgcccccaagctggagcaagtatatgcagaagtg taccgcgtgctgaagccaggagcgtacttcgcagtgtatgaggccgtgtcaaagcccatttcgacccgaaaaacaaga ggcatgtcgagataatcaacagccttgtgtatggcaatggaatcccggacatgaggacctggaaggaagctgaggagg ccggaaagaaggtcggcttcaagcttcacttctcgtatgatgctggcgaggcttcctctgtcctggcccctggtgggagcg cccgagaaacttggtcaacaccggtgtcattgcatacactaaattcgccatcaaggtgtgtgacaagattggtatcctgcca agggactatgccaagttcgccaagtgtgtgggagattgcattcctgacgccgtggaatctggagagctgggcatcttcacc ccgatgtacgtgtacgtgtggcagaagccggagaagtcaacttaa >Seq5 [*Botryococcus braunii* race B] sterol methyltransferase-like 2 (SMT-2) mRNA, complete cds (SEQ ID NO: 5)

Atggcggcagagctcatcaaggagtacgttcccattgtatcggagtatgcaccgggcctgatcgaaggtctcctatcatgg aaaggcgcagtcggcttggtcgcgccactggaattggctacgttcttatcattcaacgcttcaaaacacatctgcgacg aagaacttgtggggattgacaggaggtggtgtccaggctaaggatgtcagcaaggtcgcggacgtctacgataagtcgt acggcaaggaggggacggctccctcacccctgcaccatttggacaagaaggaatctgtggcggtcgtggacacgttcta caacctggtcacggatggctacgaggcgtgctggacaccagcttccatttctcgccgcgcccgcgattcaccaacttccg caccgctcagatcctgcacgaggctcgcatcggctacatggcccgcatccagccgggattcaaagttcttgactgcggct gtggaattgggaacccgggcaggactgtggcggctctcacaggggcccatgtgaccggcatcaccatcaatgagtacc -continued aagtcaagagagctctgtaccacaccaagaaggcgggtttgacgggattgttcacgccagtgcaaggagacttcacag acatgccttttgcggacaagactttcgatgctgctttcgccttgaggcgacctgccacgcacccaagctggagcaggtgta cggagagatcttccgcgtgctcaagccaggtgctttcttcgccgtgtacgaggccgtcaccaccgacaagttcgacccccgc caacaagcgccacgtcgagattatcaacagcctggtctacggcaacggcattccggacatgaggacatggaagcagg ctgaagaggcgggtaagaacgtgggcttcaagctgtgctgcgcatttgtgctggtgctgcttcacctgtggctctcccctgg tgggaacgcgtgaaggacatgatcaattggggcgttgtcaaatacacgaaggccgcctgcctggcgctggactccctcc gcttgctgcccaaggactactggaaagtagccaacatggtcggggacagccttcctgatctcgtcgagtctggggagacc gggatcttcacgccgatgtacctgctcgtgtggcaaaagcccgaggagtag >Seq6 [*Botryococcus braunii* race B] sterol methyltransferase-like 3 (SMT-3) mRNA, complete cds (SEQ ID NO: 6)

Atggtgtcggagcttgtatcgatgtacgttcctcctattgtagaggctgccaaagccgtaacaccatggcaagcggctgctg gggtcactgcagccattttttataggatcatatctttggcacagtgcttcgcttcgcaaacaaagacgaacaggcactgcaga cggtggactgttttcgttgaccgcaggagggattaagaagcaagacgtaacaaaactcgtagactccttcagtcaagcat acaagacggaggacgacggccagcttacatgccaccatatccaccagggagcagtccgtggaaatggtaaacaccttct atgacctgatcacggacctttatgagtgggcctgggacacaagcttccacttctcgtgccgccccagatgggccaacttcg ctcaagcccaggtcctgcacgagtggcgcattgccaatcttgctaacattcagcccggcatgaaagtccttgatgttggaac cggagttggcaacccaggcaggacgattgcctctctctctggcgcccaagtgacaggagtcaccatcaatgcatatcaag tgaagcgcgctctgcaccacaccaggaaggctaaattggaagattttttacaaaccagtgcaggccgactttactgacacg cctttcgaagatgacactttcgatgctgcttttgcaattgaagccacctgccatgccccaagctggagcaggtgtacaagg aagtgtaccgcgtgctgaagcctggagcgtacttcgctctttatgatggcgtgacaaagcccaactttgaccccaagaacg agaggcacgtgcaattgatgaacgctacggtgatcggcaacggatgcccggacatgaggacgtggaaggagtgtgag gagataggaaaggaggtcggcttcaagctgcacatgtcgtatgatgctggcgaagcttcccgcgtcctccacccctggtg ggagaaactcgacaacttcatcaacacaggctttgcgtggtatggaccggcctccattaagctcttgtcgaaaattggttttct gccaagggacttcacgaaattcatcgatattgcggcagctagtgttttctctgtcaaggaggctggagagcttggcattttca ctcccatgtacgtattcgtgtggcagaagccggagaagaccgcttga

---

The invention claimed is:

1. An expression vector comprising (i) a promoter non-native to TMT-1 and TMT-2 and a nucleic acid having (ii) a nucleic acid sequence encoding a protein selected from the group consisting of triterpene methyltransferase 1 (TMT-1) and triterpene methyltransferase 2 (TMT-2), selected from the group consisting of SEQ ID NOS: 1 and 2, wherein TMT-1 and TMT-2 have specificity for squalene and not botryococcene.

2. The expression vector of claim 1, wherein the nucleic acid sequence consists of both SEQ ID NOS: 1 and 2.

3. The expression vector of claim 1, wherein the nucleic acid further comprises a sequence encoding at least one triterpene synthase.

4. The expression vector of claim 3, wherein the at least one triterpene synthase is a squalene synthase.

5. The expression vector of claim 3, wherein the at least one triterpene synthase is from *Botryococcus braunii*.

6. The expression vector of claim 1, wherein the nucleic acid further comprises a sequence encoding prenyltransferase.

7. The expression vector of claim 1, wherein the nucleic acid comprises a chloroplast target sequence, wherein, when the nucleic acid is expressed in a plant cell with chloroplasts, the protein is directed to the chloroplasts.

8. The expression vector of claim 3, wherein the nucleic acid comprises a chloroplast target sequence, wherein, when the nucleic acid is expressed in a plant cell with chloroplasts, the least one triterpene synthase is directed to the chloroplasts.

9. A transfected cell comprising a plant cell with an expression vector comprising a nucleic acid having (i) a non-native TMT-1 or TMT-2 promoter and (ii) a nucleic acid sequence encoding a protein selected from the group consisting of triterpene methyltransferase 1 (TMT-1) and triterpene methyltransferase 2 (TMT-2), selected from the group consisting of SEQ ID NOS: 1 and 2, wherein TMT-1 and TMT-2 have specificity for squalene and not botryococcene.

10. The transfected cell of claim 9, wherein the nucleic acid comprises a chloroplast target sequence, wherein, when the nucleic acid is expressed in the plant cell, the protein is directed to its chloroplasts.

11. The transfected cell of claim 9, wherein the nucleic acid further comprises a sequence encoding at least one triterpene synthase.

12. The transfected cell of claim 11, wherein the at least one triterpene synthase is a squalene synthase.

13. The expression vector of claim 12, wherein the nucleic acid further comprises a sequence encoding prenyltransferase.

14. The transfected cell of claim 13, wherein the nucleic acid comprises at least one chloroplast target sequence, wherein, when the nucleic acid is expressed in the plant cell, the triterpene methyltransferase, the at least one triterpene synthase and the prenyltransferase are directed to its chloroplasts.

15. A method for transforming a cell comprising transfecting a plant cell with an expression vector comprising (i) a promoter not native to TMT-1 and TMT-2 and (ii) a nucleic acid having a nucleic acid sequence encoding at least one protein selected from the group consisting of triterpene methyltransferase 1 (TMT-1) and triterpene methyltransferase 2 (TMT-2), selected from the group consisting of SEQ ID NOS: 1 and 2 wherein TMT-1 and TMT-2 have specificity for squalene and not botryococcene.

16. The method of claim 15, wherein the at least one protein comprises both TMT-1 and TMT-2.

17. The method of claim 15, wherein the nucleic acid comprises a chloroplast target sequence, wherein, when the nucleic acid is expressed in the plant cell, the protein is directed to its chloroplasts.

18. The method of claim 15, wherein the nucleic acid further comprises a sequence encoding at least one triterpene synthase.

19. The method of claim 18, wherein the at least one triterpene synthase is a squalene synthase.

20. The method of claim 19, wherein the nucleic acid further comprises a sequence encoding prenyltransferase.

21. The method of claim 20, wherein the nucleic acid comprises at least one chloroplast target sequence, wherein, when the nucleic acid is expressed in the plant cell, the triterpene methyltransferase, the at least one triterpene synthase and the prenyltransferase are directed to its chloroplasts.

22. The expression vector of claim 1, wherein the nucleic acid is cDNA.

23. The expression vector of claim 1, wherein the nucleic acid is cDNA.

24. The transfected cell of claim 9, wherein the nucleic acid is cDNA.

25. The method of claim 15, wherein the nucleic acid is from cDNA.

\* \* \* \* \*

SEQUENCE LISTING

<160> NUMBER OF SEQ ID NOS: 14

<210> SEQ ID NO 1
<211> LENGTH: 1137
<212> TYPE: DNA
<213> ORGANISM: Botryococcus braunii

<400> SEQUENCE: 1

| | | | | |
|---|---|---|---|---|
| atgggattgg | atctcctttc | aacgtacgcc | ccaggcattt | tgacagtct cctgacttgg | 60 |
| aagggagtgg | ctggtttggt | cgttgccatt | accttgggct | acctgatcat atctaggctt | 120 |
| cctggacaaa | agagccgtcc | aaagctattg | gatctaaaga | caggaggtat ctcctttgag | 180 |
| aaggtcgcgg | ccgtgtatga | tgactacgac | aagtcgtacg | gggagggaga tcacggcgaa | 240 |
| ctgcatgtca | aggacaagaa | caaggtcttc | caactggcta | atactttcta cgattttgta | 300 |
| actgatggtt | acgagtgggc | atggggttcg | agcttccact | tctcccagcg catgcccggc | 360 |
| ctgtcccatg | cggcttccca | gatgctccac | gagtcgcgca | tggcatcttt tttgcgtctg | 420 |
| aagccgggaa | tgaaatgctt | ggatgtgggc | tgtggtgtgg | caacccctgg acggacagtt | 480 |
| gcgtcctgca | gtggggccga | ggtcaccggc | atcaccatca | atgagtacca gatcaagagg | 540 |

```
gcagagtacc acaacaaaag gacgggcttg gtggggtact tcaaaccagt ggtgggaaat    600
ttctgtgcca tgccattcaa ggataagact tttgatgctg ctttcgccat ggattccact    660
tgccacgcac ccaagctgga ggacgtgtac agcgaagttt tccgtgtcct gaagccagga    720
ggcctgtttg ccacatacga gtgggtctcc accaaagact acgaccccaa caactcccga    780
catgtgaaag tgatgaacag catcatcttc ggcaacggtc ttccgaacat tcggagctgg    840
aaacaggctg aggacgccgg gaaaaacgtg ggattcaagt tggtgacaag cttcgatctc    900
gccaccgccc ccccagttgg caagccctgg tactatgtgc ccgagctgat ggtgaagtat    960
gggctgctga cgattcagaa ggctctagtg cgcggagcct gcaacgtggg cctccttccc   1020
aatgagggct ggaaggtttg caacatggtc gccgacatgg ttcccaacct tgtcgagggt   1080
ggcgcgacaa acatcttcac ccccatgcac ttgctcatct ttgagaagcc caagtga      1137
```

```
<210> SEQ ID NO 2
<211> LENGTH: 1137
<212> TYPE: DNA
<213> ORGANISM: Botryococcus braunii

<400> SEQUENCE: 2
atggcagtag atttgctttc gatctatggg ccaggccttt ttgagagtct tctcacggta     60
aaaggcgcta ctggcttgat agctgctctt atcttaggat acatcataat aacaagactg    120
cctggtcaaa agactaaacc caaattactg gatttaacag cgggtggtat tccatttgag    180
aaagtcgggg aggtgtttaa tgattacgac aaatcttatg gaaagggaac ccacggcgaa    240
ttgcatgtcc aggatacaaa taaagtattc caattggcaa acacatttta cgactttgtc    300
actgatggtt acgagtgggc ctggggttcg agcttccact tctcacagcg catgcctggc    360
ttgtctcatg cagcctcgca gatgctccat gaatcacgga tggcatctta tctccgtttg    420
aagccaggga tgacatgctt agacgtgggc tgtggtgtgg gcaacccggg aagaactgta    480
gccgcatgca gtggtgcagt tgtgactgga atcactataa acaagtacca gatccaaagg    540
gctgagtacc acaacagaag gacgggcttg gtgggatttt ttaaaccaac agttggaaac    600
ttctgcaaca tgccatttga tgctaagtct tttgatgccg cttttgcaat ggatgccact    660
tgccacgccc ccaagctgga agacgtgtat ggggaggtct tccgcgtatt gaagcctgga    720
ggcttctttg ctacctatga gtgggtttct acaaagaact atgaccccac caacacgaga    780
catgtcaaag tgatgaacag tatcatcttt gggaacggtc ttccgaacat aaggagctgg    840
aaacaagctg aggaggcagg ggagaatgtg ggatttaaac tgttgacaag ttttgacctt    900
gcaacagcgc ccccagtggg aaagccctgg tattatgtgc cagagctgat ggttaagtat    960
gggcttctaa agatccagaa ggctctggtg cgcggagcct gcagcttggg tcttctcccc   1020
gaccagagct ggaaggtttg caacatggtc gctgacatgg ttcccaacct tgtcgagggt   1080
ggagcaacag acattttcac ccctatgcac ttgctgatct tccagaagcc agaatga      1137
```

```
<210> SEQ ID NO 3
<211> LENGTH: 1140
<212> TYPE: DNA
<213> ORGANISM: Botryococcus braunii

<400> SEQUENCE: 3
atggccctgg atcttctttc atcctacgct cctggcttgg tcgaaagcct gctaacatgg     60
aaaggcgcag ccggcttggc tgcagctgtt gccctgggct atattattat aagcaacctt    120
```

-continued

| | |
|---|---|
| cctggaaggc aggttgctaa gcccagcctt cttcaagtca gaactggtgg cgtcgccttc | 180 |
| gagaaggtcg ctgaggtagt tgccgactac agtgactctt acgggcaaac tgaaaagggc | 240 |
| gaactcatcg tcaaggacaa caacaagatt gtctctctcg cgaatacttt ctatgacctc | 300 |
| atcaccgatg gatatgagtg gggatggggc tccggcttcc acttctctca taggctgcca | 360 |
| gggatgtcct tcaatgcatc tcagctgctc catgagtccc gtatggcgtc tttcctgcgc | 420 |
| ctgaagcccg gcatgcaagt tcttgatgtt ggctgcggtg tcggaaaccc tggcagaacg | 480 |
| gttgctgcct gcagtggagc agtggtgact ggcatcacca tcaatgcata ccagatcaag | 540 |
| cgcgctgagt tgcacactaa gcgggcgggc ttggtaggat acttcaagcc agttcaggga | 600 |
| aacttctgcg cgatgccttt ccaagacaag agcttcgatg ctgcctttgc catggactct | 660 |
| acttgccatg cccccaagct ggaggatgtg tactccgagg tcttccgcgt gttgaagcct | 720 |
| ggcgcatact ttgcaactta tgagtgggtg tctacaaaga actacgactc caacaaccca | 780 |
| gagcacgtga agtgcatgaa cagcatcatc ctgggcaatg gcctgccgaa catcaggagt | 840 |
| tggaagcaag ctgaggaggc agggaagaac gtgggtttca acctgcttac cagcctcgac | 900 |
| atggctacaa actcccccat cggaaagccc tggtactctg tcccagagcg catggtaaac | 960 |
| tggggcctgt tccgtttcca caaggcttgc attcgcactg cctctaccct gcatctgctg | 1020 |
| ccgccagaat cctggaagtt cttctacatc cttgcagaga tggccgagaa ccttgtaaag | 1080 |
| ggtgggcaat gggacatctt cacccccatg cacttgctga tcttccaaaa gccagagtaa | 1140 |

<210> SEQ ID NO 4
<211> LENGTH: 1170
<212> TYPE: DNA
<213> ORGANISM: Botryococcus braunii

<400> SEQUENCE: 4

| | |
|---|---|
| atggcgtccg agctcttcgc gacatactac cctcgcgtgg tagaggccgc tcagcaactc | 60 |
| gcaccatggc aaatcgctgc tggagtaacc gcggccgttg ttattggtgg ctatatatgg | 120 |
| atcatcacag agcttcgtag ccctcgacga acaggaacta gtctgttcaa attgtccgga | 180 |
| ggtggtatta gaagcacga tgtagcaaaa ttcatggacg gctacgagaa atcatacaaa | 240 |
| actcaggaag acggtgcgct gacatggcac cacatcagca aggaggactc tgtcaagatg | 300 |
| gtgaacacct tctacgacct ggtcacagac gcgtatgagt gggcctggga catctctttc | 360 |
| cacttctcct gccgacctgt gtgggccaac tttgcccagg cccaagttct ccatgagtgc | 420 |
| cgcattgcca acctggctcg catccaacct ggcatgaaag ttattgatgt tggcactgga | 480 |
| gtgggcaacc ccggccggac cattgcatca ctgacggggg cccatgtgac cggtgtcacc | 540 |
| atcaacgcat accagattaa gcgggcgctg caccacacaa agaaggctgg cctgttggac | 600 |
| atgtacaaac cagtgcaggc tgatttcacc gacatgcctt cgccgacga gagttttgat | 660 |
| gctgccttcg caattgaagc cacctgccac gcccccaagc tggagcaagt atatgcagaa | 720 |
| gtgtaccgcg tgctgaagcc aggagcgtac ttcgcagtgt atgaggccgt gtcaaagccc | 780 |
| aatttcgacc cgaaaaacaa gaggcatgtc gagataatca cagccttgt gtatggcaat | 840 |
| ggaatcccgg acatgaggac ctggaaggaa gctgaggagg ccggaaagaa ggtcggcttc | 900 |
| aagcttcact tctcgtatga tgctggcgag gcttcctctg tcctggcccc ctggtgggag | 960 |
| cgcccgagaa acttggtcaa caccggtgtc attgcataca ctaaattcgc catcaaggtg | 1020 |
| tgtgacaaga ttggtatcct gccaagggac tatgccaagt cgccaagtg tgtgggagat | 1080 |
| tgcattcctg acgccgtgga atctggagag ctgggcatct tcacccgat gtacgtgtac | 1140 |

-continued gtgtggcaga agccggagaa gtcaacttaa 1170

<210> SEQ ID NO 5
<211> LENGTH: 1170
<212> TYPE: DNA
<213> ORGANISM: Botryococcus braunii

<400> SEQUENCE: 5
atggcggcag agctcatcaa ggagtacgtt cccattgtat cggagtatgc accgggcctg 60
atcgaaggtc tcctatcatg gaaaggcgca gtcggcttgg tcgcggccac tggaattggc 120
tacgttctta tcattcaacg gcttcaaaac acatctgcga cgaagaactt gtggggattg 180
acaggaggtg gtgtccaggc taaggatgtc agcaaggtcg cggacgtcta cgataagtcg 240
tacggcaagg agggggacgg ctccctcacc ctgcaccatt tggacaagaa ggaatctgtg 300
gcggtcgtgg acacgttcta caacctggtc acggatggct acgaggcgtg ctgggacacc 360
agcttccatt tctcgccgcg cccgcgattc accaacttcc gcaccgctca gatcctgcac 420
gaggctcgca tcggctacat ggcccgcatc cagccgggat tcaaagttct tgactgcggc 480
tgtggaattg ggaacccggg caggactgtg gcggctctca caggggccca tgtgaccggc 540
atcaccatca atgagtacca agtcaagaga gctctgtacc acaccaagaa ggcgggtttg 600
acgggattgt tcacgccagt gcaaggagac ttcacagaca tgccttttgc ggacaagact 660
ttcgatgctg ctttcgccat tgaggcgacc tgccacgcac ccaagctgga gcaggtgtac 720
ggagagatct tccgcgtgct caagccaggt gctttcttcg ccgtgtacga ggccgtcacc 780
accgacaagt tcgaccccgc caacaagcgc cacgtcgaga ttatcaacag cctggtctac 840
ggcaacggca ttccggacat gaggacatgg aagcaggctg aagaggcggg taagaacgtg 900
ggcttcaagc tgtgctgcgc atttgatgct ggtgctgctt cacctgtggc tctcccctgg 960
tgggaacgcg tgaaggacat gatcaattgg ggcgttgtca aatacacgaa ggccgcctgc 1020
ctggcgctgg actccctccg cttgctgccc aaggactact ggaaagtagc caacatggtc 1080
ggggacagcc ttcctgatct cgtcgagtct ggggagaccg ggatcttcac gccgatgtac 1140
ctgctcgtgt ggcaaaagcc cgaggagtag 1170

<210> SEQ ID NO 6
<211> LENGTH: 1179
<212> TYPE: DNA
<213> ORGANISM: Botryococcus braunii

<400> SEQUENCE: 6
atggtgtcgg agcttgtatc gatgtacgtt cctcctattg tagaggctgc caaagccgta 60
acaccatggc aagcggctgc tggggtcact gcagccattt ttataggatc atatctttgg 120
cacagtgctt cgcttcgcaa acaaagacga acaggcactg cagacggtgg actgttttcg 180
ttgaccgcag gagggattaa gaagcaagac gtaacaaaac tcgtagactc cttcagtcaa 240
gcatacaaga cggaggacga cggccagctt acatgccacc atatcaccag ggagcagtcc 300
gtggaaatgg taaacacctt ctatgacctg atcacggacc tttatgagtg ggcctgggac 360
acaagcttcc acttctcgtg ccgccccaga tgggccaact tcgctcaagc ccaggtcctg 420
cacgagtggc gcattgccaa tcttgctaac attcagcccg gcatgaaagt ccttgatgtt 480
ggaaccggag ttggcaaccc aggcaggacg attgcctctc tctctggcgc ccaagtgaca 540
ggagtcacca tcaatgcata tcaagtgaag cgcgctctgc accacaccag gaaggctaaa 600

```
ttggaagatt tttacaaacc agtgcaggcc gactttactg acacgccttt cgaagatgac    660
actttcgatg ctgcttttgc aattgaagcc acctgccatg ccccaagct ggagcaggtg    720 tacaaggaag tgtaccgcgt gctgaagcct ggagcgtact tcgctcttta tgatggcgtg    780
acaaagccca actttgaccc caagaacgag aggcacgtgc aattgatgaa cgctacggtg    840
atcggcaacg gatgccgga catgaggacg tggaaggagt gtgaggagat aggaaaggag    900
gtcggcttca agctgcacat gtcgtatgat gctggcgaag cttcccgcgt cctccacccc    960
tggtgggaga aactcgacaa cttcatcaac acaggctttg cgtggtatgg accggcctcc   1020
attaagctct tgtcgaaaat tggttttctg ccaagggact tcacgaaatt catcgatatt   1080
gcggcagcta gtgttttctc tgtcaaggag gctggagagc ttggcatttt cactcccatg   1140
tacgtattcg tgtggcagaa gccggagaag accgcttga                          1179
```

<210> SEQ ID NO 7
<211> LENGTH: 378
<212> TYPE: PRT
<213> ORGANISM: Botryococcus braunii

<400> SEQUENCE: 7

```
Met Gly Leu Asp Leu Leu Ser Thr Tyr Ala Pro Gly Ile Phe Asp Ser
1               5                   10                  15

Leu Leu Thr Trp Lys Gly Val Ala Gly Leu Val Val Ala Ile Thr Leu
            20                  25                  30

Gly Tyr Leu Ile Ile Ser Arg Leu Pro Gly Gln Lys Ser Arg Pro Lys
        35                  40                  45

Leu Leu Asp Leu Lys Thr Gly Gly Ile Ser Phe Glu Lys Val Ala Ala
    50                  55                  60

Val Tyr Asp Asp Tyr Asp Lys Ser Tyr Gly Glu Gly Asp His Gly Glu
65                  70                  75                  80

Leu His Val Lys Asp Lys Asn Lys Val Phe Gln Leu Ala Asn Thr Phe
                85                  90                  95

Tyr Asp Phe Val Thr Asp Gly Tyr Glu Trp Ala Trp Gly Ser Ser Phe
            100                 105                 110

His Phe Ser Gln Arg Met Pro Gly Leu Ser His Ala Ala Ser Gln Met
        115                 120                 125

Leu His Glu Ser Arg Met Ala Ser Phe Leu Arg Leu Lys Pro Gly Met
    130                 135                 140

Lys Cys Leu Asp Val Gly Cys Gly Val Gly Asn Pro Gly Arg Thr Val
145                 150                 155                 160

Ala Ser Cys Ser Gly Ala Glu Val Thr Gly Ile Thr Ile Asn Glu Tyr
                165                 170                 175

Gln Ile Lys Arg Ala Glu Tyr His Asn Lys Arg Thr Gly Leu Val Gly
            180                 185                 190

Tyr Phe Lys Pro Val Val Gly Asn Phe Cys Ala Met Pro Phe Lys Asp
        195                 200                 205

Lys Thr Phe Asp Ala Ala Phe Ala Met Asp Ser Thr Cys His Ala Pro
    210                 215                 220

Lys Leu Glu Asp Val Tyr Ser Glu Val Phe Arg Val Leu Lys Pro Gly
225                 230                 235                 240

Gly Leu Phe Ala Thr Tyr Glu Trp Val Ser Thr Lys Asp Tyr Asp Pro
                245                 250                 255

Asn Asn Ser Arg His Val Lys Val Met Asn Ser Ile Ile Phe Gly Asn
            260                 265                 270
```

```
Gly Leu Pro Asn Ile Arg Ser Trp Lys Gln Ala Glu Asp Ala Gly Lys
            275                 280                 285

Asn Val Gly Phe Lys Leu Val Thr Ser Phe Asp Leu Ala Thr Ala Pro
        290                 295                 300

Pro Val Gly Lys Pro Trp Tyr Tyr Val Pro Glu Leu Met Val Lys Tyr
305                 310                 315                 320

Gly Leu Leu Thr Ile Gln Lys Ala Leu Val Arg Gly Ala Cys Asn Val
                325                 330                 335

Gly Leu Leu Pro Asn Glu Gly Trp Lys Val Cys Asn Met Val Ala Asp
            340                 345                 350

Met Val Pro Asn Leu Val Glu Gly Ala Thr Asn Ile Phe Thr Pro
        355                 360                 365

Met His Leu Leu Ile Phe Glu Lys Pro Lys
    370                 375

<210> SEQ ID NO 8
<211> LENGTH: 378
<212> TYPE: PRT
<213> ORGANISM: Botryococcus braunii

<400> SEQUENCE: 8

Met Ala Val Asp Leu Leu Ser Ile Tyr Gly Pro Gly Leu Phe Glu Ser
1               5                   10                  15

Leu Leu Thr Val Lys Gly Ala Thr Gly Leu Ile Ala Ala Leu Ile Leu
            20                  25                  30

Gly Tyr Ile Ile Ile Thr Arg Leu Pro Gly Gln Lys Thr Lys Pro Lys
        35                  40                  45

Leu Leu Asp Leu Thr Ala Gly Gly Ile Pro Phe Glu Lys Val Gly Glu
    50                  55                  60

Val Phe Asn Asp Tyr Asp Lys Ser Tyr Gly Lys Gly Thr His Gly Glu
65                  70                  75                  80

Leu His Val Gln Asp Thr Asn Lys Val Phe Gln Leu Ala Asn Thr Phe
                85                  90                  95

Tyr Asp Phe Val Thr Asp Gly Tyr Glu Trp Ala Trp Gly Ser Ser Phe
            100                 105                 110

His Phe Ser Gln Arg Met Pro Gly Leu Ser His Ala Ala Ser Gln Met
        115                 120                 125

Leu His Glu Ser Arg Met Ala Ser Tyr Leu Arg Leu Lys Pro Gly Met
    130                 135                 140

Thr Cys Leu Asp Val Gly Cys Gly Val Gly Asn Pro Gly Arg Thr Val
145                 150                 155                 160

Ala Ala Cys Ser Gly Ala Val Val Thr Gly Ile Thr Ile Asn Lys Tyr
                165                 170                 175

Gln Ile Gln Arg Ala Glu Tyr His Asn Arg Arg Thr Gly Leu Val Gly
            180                 185                 190

Phe Phe Lys Pro Thr Val Gly Asn Phe Cys Asn Met Pro Phe Asp Ala
        195                 200                 205

Lys Ser Phe Asp Ala Ala Phe Ala Met Asp Ala Thr Cys His Ala Pro
    210                 215                 220

Lys Leu Glu Asp Val Tyr Gly Glu Val Phe Arg Val Leu Lys Pro Gly
225                 230                 235                 240

Gly Phe Phe Ala Thr Tyr Glu Trp Val Ser Thr Lys Asn Tyr Asp Pro
                245                 250                 255

Thr Asn Thr Arg His Val Lys Val Met Asn Ser Ile Ile Phe Gly Asn
            260                 265                 270
```

```
Gly Leu Pro Asn Ile Arg Ser Trp Lys Gln Ala Glu Ala Gly Glu
        275                 280                 285

Asn Val Gly Phe Lys Leu Leu Thr Ser Phe Asp Leu Ala Thr Ala Pro
    290                 295                 300

Pro Val Gly Lys Pro Trp Tyr Tyr Val Pro Glu Leu Met Val Lys Tyr
305                 310                 315                 320

Gly Leu Leu Lys Ile Gln Lys Ala Leu Val Arg Gly Ala Cys Ser Leu
                325                 330                 335

Gly Leu Leu Pro Asp Gln Ser Trp Lys Val Cys Asn Met Val Ala Asp
                340                 345                 350

Met Val Pro Asn Leu Val Glu Gly Gly Ala Thr Asp Ile Phe Thr Pro
            355                 360                 365

Met His Leu Leu Ile Phe Gln Lys Pro Glu
    370                 375

<210> SEQ ID NO 9
<211> LENGTH: 379
<212> TYPE: PRT
<213> ORGANISM: Botryococcus braunii

<400> SEQUENCE: 9

Met Ala Leu Asp Leu Leu Ser Ser Tyr Ala Pro Gly Leu Val Glu Ser
1               5                   10                  15

Leu Leu Thr Trp Lys Gly Ala Ala Gly Leu Ala Ala Ala Val Ala Leu
            20                  25                  30

Gly Tyr Ile Ile Ile Ser Asn Leu Pro Gly Arg Gln Val Ala Lys Pro
        35                  40                  45

Ser Leu Leu Gln Val Arg Thr Gly Gly Val Ala Phe Glu Lys Val Ala
    50                  55                  60

Glu Val Val Ala Asp Tyr Ser Asp Ser Tyr Gly Gln Thr Glu Lys Gly
65                  70                  75                  80

Glu Leu Ile Val Lys Asp Asn Asn Lys Ile Val Ser Leu Ala Asn Thr
                85                  90                  95

Phe Tyr Asp Leu Ile Thr Asp Gly Tyr Glu Trp Gly Trp Gly Ser Gly
            100                 105                 110

Phe His Phe Ser His Arg Leu Pro Gly Met Ser Phe Asn Ala Ser Gln
        115                 120                 125

Leu Leu His Glu Ser Arg Met Ala Ser Phe Leu Arg Leu Lys Pro Gly
    130                 135                 140

Met Gln Val Leu Asp Val Gly Cys Gly Val Gly Asn Pro Gly Arg Thr
145                 150                 155                 160

Val Ala Ala Cys Ser Gly Ala Val Val Thr Gly Ile Thr Ile Asn Ala
                165                 170                 175

Tyr Gln Ile Lys Arg Ala Glu Leu His Thr Lys Arg Ala Gly Leu Val
            180                 185                 190

Gly Tyr Phe Lys Pro Val Gln Gly Asn Phe Cys Ala Met Pro Phe Gln
        195                 200                 205

Asp Lys Ser Phe Asp Ala Ala Phe Ala Met Asp Ser Thr Cys His Ala
    210                 215                 220

Pro Lys Leu Glu Asp Val Tyr Ser Glu Val Phe Arg Val Leu Lys Pro
225                 230                 235                 240

Gly Ala Tyr Phe Ala Thr Tyr Glu Trp Val Ser Thr Lys Asn Tyr Asp
                245                 250                 255

Ser Asn Asn Pro Glu His Val Lys Cys Met Asn Ser Ile Ile Leu Gly
```

```
            260                 265                 270
Asn Gly Leu Pro Asn Ile Arg Ser Trp Lys Gln Ala Glu Glu Ala Gly
            275                 280                 285

Lys Asn Val Gly Phe Asn Leu Leu Thr Ser Leu Asp Met Ala Thr Asn
            290                 295                 300

Ser Pro Ile Gly Lys Pro Trp Tyr Ser Val Pro Glu Arg Met Val Asn
305                 310                 315                 320

Trp Gly Leu Phe Arg Phe His Lys Ala Cys Ile Arg Thr Ala Ser Thr
                325                 330                 335

Leu His Leu Leu Pro Pro Glu Ser Trp Lys Phe Phe Tyr Ile Leu Ala
                340                 345                 350

Glu Met Ala Glu Asn Leu Val Lys Gly Gly Gln Trp Asp Ile Phe Thr
            355                 360                 365

Pro Met His Leu Leu Ile Phe Gln Lys Pro Glu
            370                 375

<210> SEQ ID NO 10
<211> LENGTH: 389
<212> TYPE: PRT
<213> ORGANISM: Botryococcus braunii

<400> SEQUENCE: 10

Met Ala Ser Glu Leu Phe Ala Thr Tyr Tyr Pro Arg Val Val Glu Ala
1               5                   10                  15

Ala Gln Gln Leu Ala Pro Trp Gln Ile Ala Ala Gly Val Thr Ala Ala
            20                  25                  30

Val Val Ile Gly Gly Tyr Ile Trp Ile Ile Thr Glu Leu Arg Ser Pro
        35                  40                  45

Arg Arg Thr Gly Thr Ser Leu Phe Lys Leu Ser Gly Gly Ile Lys
50                  55                  60

Lys His Asp Val Ala Lys Phe Met Asp Gly Tyr Glu Lys Ser Tyr Lys
65                  70                  75                  80

Thr Gln Glu Asp Gly Ala Leu Thr Trp His His Ile Ser Lys Glu Asp
                85                  90                  95

Ser Val Lys Met Val Asn Thr Phe Tyr Asp Leu Val Thr Asp Ala Tyr
            100                 105                 110

Glu Trp Ala Trp Asp Ile Ser Phe His Phe Ser Cys Arg Pro Val Trp
        115                 120                 125

Ala Asn Phe Ala Gln Ala Gln Val Leu His Glu Cys Arg Ile Ala Asn
130                 135                 140

Leu Ala Arg Ile Gln Pro Gly Met Lys Val Ile Asp Val Gly Thr Gly
145                 150                 155                 160

Val Gly Asn Pro Gly Arg Thr Ile Ala Ser Leu Thr Gly Ala His Val
                165                 170                 175

Thr Gly Val Thr Ile Asn Ala Tyr Gln Ile Lys Arg Ala Leu His His
            180                 185                 190

Thr Lys Lys Ala Gly Leu Leu Asp Met Tyr Lys Pro Val Gln Ala Asp
        195                 200                 205

Phe Thr Asp Met Pro Phe Ala Asp Glu Ser Phe Asp Ala Ala Phe Ala
    210                 215                 220

Ile Glu Ala Thr Cys His Ala Pro Lys Leu Glu Gln Val Tyr Ala Glu
225                 230                 235                 240

Val Tyr Arg Val Leu Lys Pro Gly Ala Tyr Phe Ala Val Tyr Glu Ala
                245                 250                 255
```

```
Val Ser Lys Pro Asn Phe Asp Pro Lys Asn Lys Arg His Val Glu Ile
            260                 265                 270

Ile Asn Ser Leu Val Tyr Gly Asn Gly Ile Pro Asp Met Arg Thr Trp
            275                 280                 285

Lys Glu Ala Glu Ala Gly Lys Lys Val Gly Phe Lys Leu His Phe
    290                 295                 300

Ser Tyr Asp Ala Gly Glu Ala Ser Ser Val Leu Ala Pro Trp Trp Glu
305                 310                 315                 320

Arg Pro Arg Asn Leu Val Asn Thr Gly Val Ile Ala Tyr Thr Lys Phe
                325                 330                 335

Ala Ile Lys Val Cys Asp Lys Ile Gly Ile Leu Pro Arg Asp Tyr Ala
            340                 345                 350

Lys Phe Ala Lys Cys Val Gly Asp Cys Ile Pro Asp Ala Val Glu Ser
            355                 360                 365

Gly Glu Leu Gly Ile Phe Thr Pro Met Tyr Val Tyr Val Trp Gln Lys
    370                 375                 380

Pro Glu Lys Ser Thr
385

<210> SEQ ID NO 11
<211> LENGTH: 389
<212> TYPE: PRT
<213> ORGANISM: Botryococcus braunii

<400> SEQUENCE: 11

Met Ala Ala Glu Leu Ile Lys Glu Tyr Val Pro Ile Val Ser Glu Tyr
1               5                   10                  15

Ala Pro Gly Leu Ile Glu Gly Leu Leu Ser Trp Lys Gly Ala Val Gly
            20                  25                  30

Leu Val Ala Ala Thr Gly Ile Gly Tyr Val Leu Ile Ile Gln Arg Leu
        35                  40                  45

Gln Asn Thr Ser Ala Thr Lys Asn Leu Trp Gly Leu Thr Gly Gly Gly
50                  55                  60

Val Gln Ala Lys Asp Val Ser Lys Val Ala Asp Val Tyr Asp Lys Ser
65                  70                  75                  80

Tyr Gly Lys Glu Gly Asp Gly Ser Leu Thr Leu His His Leu Asp Lys
                85                  90                  95

Lys Glu Ser Val Ala Val Asp Thr Phe Tyr Asn Leu Val Thr Asp
            100                 105                 110

Gly Tyr Glu Ala Cys Trp Asp Thr Ser Phe His Phe Ser Pro Arg Pro
        115                 120                 125

Arg Phe Thr Asn Phe Arg Thr Ala Gln Ile Leu His Glu Ala Arg Ile
130                 135                 140

Gly Tyr Met Ala Arg Ile Gln Pro Gly Phe Lys Val Leu Asp Cys Gly
145                 150                 155                 160

Cys Gly Ile Gly Asn Pro Gly Arg Thr Val Ala Ala Leu Thr Gly Ala
                165                 170                 175

His Val Thr Gly Ile Thr Ile Asn Glu Tyr Gln Val Lys Arg Ala Leu
            180                 185                 190

Tyr His Thr Lys Lys Ala Gly Leu Thr Gly Leu Phe Thr Pro Val Gln
        195                 200                 205

Gly Asp Phe Thr Asp Met Pro Phe Ala Asp Lys Thr Phe Asp Ala Ala
    210                 215                 220

Phe Ala Ile Glu Ala Thr Cys His Ala Pro Lys Leu Glu Gln Val Tyr
225                 230                 235                 240
```

```
Gly Glu Ile Phe Arg Val Leu Lys Pro Gly Ala Phe Ala Val Tyr
            245                 250                 255

Glu Ala Val Thr Thr Asp Lys Phe Asp Pro Ala Asn Lys Arg His Val
                260                 265                 270

Glu Ile Ile Asn Ser Leu Val Tyr Gly Asn Gly Ile Pro Asp Met Arg
            275                 280                 285

Thr Trp Lys Gln Ala Glu Glu Ala Gly Lys Asn Val Gly Phe Lys Leu
        290                 295                 300

Cys Cys Ala Phe Asp Ala Gly Ala Ala Ser Pro Val Ala Leu Pro Trp
305                 310                 315                 320

Trp Glu Arg Val Lys Asp Met Ile Asn Trp Gly Val Val Lys Tyr Thr
                325                 330                 335

Lys Ala Ala Cys Leu Ala Leu Asp Ser Leu Arg Leu Leu Pro Lys Asp
            340                 345                 350

Tyr Trp Lys Val Ala Asn Met Val Gly Asp Ser Leu Pro Asp Leu Val
        355                 360                 365

Glu Ser Gly Glu Thr Gly Ile Phe Thr Pro Met Tyr Leu Leu Val Trp
370                 375                 380

Gln Lys Pro Glu Glu
385

<210> SEQ ID NO 12
<211> LENGTH: 392
<212> TYPE: PRT
<213> ORGANISM: Botryococcus braunii

<400> SEQUENCE: 12

Met Val Ser Glu Leu Val Ser Met Tyr Val Pro Pro Ile Val Glu Ala
1               5                   10                  15

Ala Lys Ala Val Thr Pro Trp Gln Ala Ala Gly Val Thr Ala Ala
            20                  25                  30

Ile Phe Ile Gly Ser Tyr Leu Trp His Ser Ala Ser Leu Arg Lys Gln
            35                  40                  45

Arg Arg Thr Gly Thr Ala Asp Gly Gly Leu Phe Ser Leu Thr Ala Gly
        50                  55                  60

Gly Ile Lys Lys Gln Asp Val Thr Lys Leu Val Asp Ser Phe Ser Gln
65                  70                  75                  80

Ala Tyr Lys Thr Glu Asp Asp Gly Gln Leu Thr Cys His His Ile Thr
                85                  90                  95

Arg Glu Gln Ser Val Glu Met Val Asn Thr Phe Tyr Asp Leu Ile Thr
            100                 105                 110

Asp Leu Tyr Glu Trp Ala Trp Asp Thr Ser Phe His Phe Ser Cys Arg
        115                 120                 125

Pro Arg Trp Ala Asn Phe Ala Gln Ala Gln Val Leu His Glu Trp Arg
130                 135                 140

Ile Ala Asn Leu Ala Asn Ile Gln Pro Gly Met Lys Val Leu Asp Val
145                 150                 155                 160

Gly Thr Gly Val Gly Asn Pro Gly Arg Thr Ile Ala Ser Leu Ser Gly
                165                 170                 175

Ala Gln Val Thr Gly Val Thr Ile Asn Ala Tyr Gln Val Lys Arg Ala
            180                 185                 190

Leu His His Thr Arg Lys Ala Lys Leu Glu Asp Phe Tyr Lys Pro Val
        195                 200                 205

Gln Ala Asp Phe Thr Asp Thr Pro Phe Glu Asp Asp Thr Phe Asp Ala
```

```
                    210                 215                 220
Ala Phe Ala Ile Glu Ala Thr Cys His Ala Pro Lys Leu Glu Gln Val
225                 230                 235                 240

Tyr Lys Glu Val Tyr Arg Val Leu Lys Pro Gly Ala Tyr Phe Ala Leu
                245                 250                 255

Tyr Asp Gly Val Thr Lys Pro Asn Phe Asp Pro Lys Asn Glu Arg His
            260                 265                 270

Val Gln Leu Met Asn Ala Thr Val Ile Gly Asn Gly Cys Pro Asp Met
        275                 280                 285

Arg Thr Trp Lys Glu Cys Glu Glu Ile Gly Lys Glu Val Gly Phe Lys
    290                 295                 300

Leu His Met Ser Tyr Asp Ala Gly Glu Ala Ser Arg Val Leu His Pro
305                 310                 315                 320

Trp Trp Glu Lys Leu Asp Asn Phe Ile Asn Thr Gly Phe Ala Trp Tyr
                325                 330                 335

Gly Pro Ala Ser Ile Lys Leu Leu Ser Lys Ile Gly Phe Leu Pro Arg
            340                 345                 350

Asp Phe Thr Lys Phe Ile Asp Ile Ala Ala Ala Ser Val Phe Ser Val
        355                 360                 365

Lys Glu Ala Gly Glu Leu Gly Ile Phe Thr Pro Met Tyr Val Phe Val
    370                 375                 380

Trp Gln Lys Pro Glu Lys Thr Ala
385                 390

<210> SEQ ID NO 13
<211> LENGTH: 387
<212> TYPE: PRT
<213> ORGANISM: Chlamydomonas reinhardtii

<400> SEQUENCE: 13

Met Ala Val Ala Leu Pro Ala Ala Val Thr Ser Ala Tyr Glu Arg Leu
1               5                   10                  15

Ala Gly Glu Phe Asp Lys Leu Ser Thr Thr Gln Lys Tyr Ala Val Gly
            20                  25                  30

Ile Ala Gly Gly Val Thr Ser Leu Tyr Leu Leu Ala Lys Val Leu Lys
        35                  40                  45

Gly Ser Asp Arg Asp Lys Pro Thr Thr Leu Gln Leu Ser Gly Gly Ser
    50                  55                  60

Ile Asp Ser Ser Lys Val Lys Asp Glu Phe Thr Ala Tyr Ala Asp Ser
65                  70                  75                  80

Tyr Gly Lys Asn Ala Gly Glu Gly Ile Thr Asp Arg Ser Lys Thr Val
                85                  90                  95

His Leu Val Asp Val Phe Tyr Ser Leu Val Thr Asp Ile Tyr Glu Trp
            100                 105                 110

Gly Trp Gly Gln Ser Phe His Phe Ser Pro Lys Leu Pro Asn Lys Asp
        115                 120                 125

Leu Lys Ala Ser Glu Ala Ala His Glu Ala Arg Ile Ala Ala Leu Leu
    130                 135                 140

Arg Leu Gln Pro Gly Gln Lys Ala Leu Asp Cys Gly Cys Gly Val Gly
145                 150                 155                 160

Gly Pro Met Arg Thr Val Ala Ala Val Ser Gly Ala His Ile Thr Gly
                165                 170                 175

Ile Thr Ile Asn Gln Tyr Gln Val Asp Arg Ala Lys Thr His Asn Ala
            180                 185                 190
```

```
Arg Gln Gly Leu Ala Pro Leu Thr Asp Val Val Arg Gly Asp Phe Thr
            195                 200                 205

Asn Met Pro Phe Lys Glu Asn Thr Phe Asp Gly Ala Tyr Ala Ile Glu
210                 215                 220

Ala Thr Cys His Ala Pro Lys Leu Glu Gln Val Tyr Gly Glu Ile Tyr
225                 230                 235                 240

Arg Val Leu Lys Pro Gly Ser Tyr Phe Val Ser Tyr Glu Trp Val Ser
            245                 250                 255

Thr Gln Lys Phe Asp Val Asn Asn Ala Glu His Val Lys Ile Met Asp
            260                 265                 270

Glu Ile Asn Phe Gly Asn Gly Leu Pro Glu Met Arg Thr Trp Lys Glu
            275                 280                 285

Ala Glu Asp Ala Gly Lys Asn Val Gly Phe Glu Leu Val Met Ser Leu
290                 295                 300

Asp Leu Ala Thr Ala Ser Val Val Ala Gly Pro Trp Tyr Glu Arg Leu
305                 310                 315                 320

Arg Met Gly Lys Tyr Thr His Ala Ile Asn His Gly Ile Val Ser Thr
            325                 330                 335

Val Asp Ala Leu Gly Leu Ala Pro Lys Gly Leu Lys Glu Val His His
            340                 345                 350

Met Leu Val Glu Val Ala Lys Ser Leu Ile Gln Gly Gly Glu Ser Gly
            355                 360                 365

Ile Phe Thr Pro Met His Leu Leu Phe Arg Lys Pro Gly Ala Asp
            370                 375                 380

Lys Lys Lys
385

<210> SEQ ID NO 14
<211> LENGTH: 336
<212> TYPE: PRT
<213> ORGANISM: Arabidopsis thaliana

<400> SEQUENCE: 14

Met Asp Leu Ala Ser Asn Leu Gly Gly Lys Ile Asp Lys Ser Asp Val
1               5                   10                  15

Leu Thr Ala Val Glu Lys Tyr Glu Gln Tyr His Val Phe His Gly Gly
            20                  25                  30

Asn Glu Glu Glu Arg Lys Ala Asn Tyr Thr Asp Met Val Asn Lys Tyr
            35                  40                  45

Tyr Asp Leu Ala Thr Ser Phe Tyr Glu Tyr Gly Trp Gly Glu Ser Phe
50                  55                  60

His Phe Ala Gln Arg Trp Lys Gly Glu Ser Leu Arg Glu Ser Ile Lys
65                  70                  75                  80

Arg His Glu His Phe Leu Ala Leu Gln Leu Gly Ile Gln Pro Gly Gln
            85                  90                  95

Lys Val Leu Asp Val Gly Cys Gly Ile Gly Gly Pro Leu Arg Glu Ile
            100                 105                 110

Ala Arg Phe Ser Asn Ser Val Val Thr Gly Leu Asn Asn Asn Glu Tyr
            115                 120                 125

Gln Ile Thr Arg Gly Lys Glu Leu Asn Arg Leu Ala Gly Val Asp Lys
            130                 135                 140

Thr Cys Asn Phe Val Lys Ala Asp Phe Met Lys Met Pro Phe Pro Glu
145                 150                 155                 160

Asn Ser Phe Asp Ala Val Tyr Ala Ile Glu Ala Thr Cys His Ala Pro
            165                 170                 175
```

```
Asp Ala Tyr Gly Cys Tyr Lys Glu Ile Tyr Arg Val Leu Lys Pro Gly
            180                 185                 190

Gln Cys Phe Ala Ala Tyr Glu Trp Cys Met Thr Asp Ala Phe Asp Pro
        195                 200                 205

Asp Asn Ala Glu His Gln Lys Ile Lys Gly Glu Ile Glu Ile Gly Asp
    210                 215                 220

Gly Leu Pro Asp Ile Arg Leu Thr Thr Lys Cys Leu Glu Ala Leu Lys
225                 230                 235                 240

Gln Ala Gly Phe Glu Val Ile Trp Glu Lys Asp Leu Ala Lys Asp Ser
                245                 250                 255

Pro Val Pro Trp Tyr Leu Pro Leu Asp Lys Asn His Phe Ser Leu Ser
            260                 265                 270

Ser Phe Arg Leu Thr Ala Val Gly Arg Phe Ile Thr Lys Asn Met Val
        275                 280                 285

Lys Ile Leu Glu Tyr Ile Arg Leu Ala Pro Gln Gly Ser Gln Arg Val
    290                 295                 300

Ser Asn Phe Leu Glu Gln Ala Ala Glu Gly Leu Val Asp Gly Gly Arg
305                 310                 315                 320

Arg Glu Ile Phe Thr Pro Met Tyr Phe Phe Leu Ala Arg Lys Pro Glu
                325                 330                 335
```